US009611232B2

(12) United States Patent
Green et al.

(10) Patent No.: US 9,611,232 B2
(45) Date of Patent: Apr. 4, 2017

(54) OXAZOLIDINONE AND IMIDAZOLIDINONE COMPOUNDS

(71) Applicant: Hoffmann-La Roche Inc., Little Falls, NJ (US)

(72) Inventors: Luke Green, Basel (CH); Haiyan Wang, Allschwil (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/699,144

(22) Filed: Apr. 29, 2015

(65) Prior Publication Data

US 2015/0246894 A1 Sep. 3, 2015

Related U.S. Application Data

(63) Continuation of application No. PCT/EP2013/072361, filed on Oct. 25, 2013.

(30) Foreign Application Priority Data

Oct. 29, 2012 (EP) .................................... 12190319

(51) Int. Cl.
| C07D 263/20 | (2006.01) |
| C07D 413/04 | (2006.01) |
| C07D 413/06 | (2006.01) |
| C07D 263/32 | (2006.01) |

(52) U.S. Cl.
CPC ......... *C07D 263/20* (2013.01); *C07D 263/32* (2013.01); *C07D 413/04* (2013.01); *C07D 413/06* (2013.01)

(58) Field of Classification Search
CPC .. C07D 263/20; C07D 413/04; C07D 263/32; C07D 413/06
See application file for complete search history.

(56) References Cited

U.S. PATENT DOCUMENTS 4,139,538 A * 2/1979 Kollensperger ..... C07D 263/20 548/216
4,831,026 A * 5/1989 Fujii .................... C07D 498/04 514/210.07

FOREIGN PATENT DOCUMENTS

| EP | 1 254 895 A1 | 11/2002 |
| WO | 00/34248 A1 | 6/2000 |
| WO | 02/42299 A1 | 5/2002 |
| WO | 2006/015159 A2 | 2/2006 |
| WO | 2007/109098 A2 | 9/2007 |
| WO | 2010/066840 A1 | 6/2010 |
| WO | 2010/123997 A1 | 10/2010 |

OTHER PUBLICATIONS

Delaunay et al. Journal of the Chemical Society Perkin Trans 1: Organic and Bio-Organic Chemistry, issue: 20, p. 3041-3042 (1994)).*

CAS Registry Database, 1026897-75-5, Jun. 10, 2008 (Jun. 10, 2008), Database Chemspider (Chemzoo, Inc.): XP002712597.
CAS Registry Database, 1027988-84-6, Jun. 13, 2008 (Jun. 13, 2008) , Database: Chemspider (Chemzoo, Inc) XP002712596.
CAS Registry Database, 1391422-81-3, Aug. 15, 2012 (Aug. 15, 2012), Chemical Catalog; Supplier: aLphachiron Biochemicals LTC: XP002712595.
CAS Registry Database, 1993:408719, Conjugate addition of organocuprates to methyl crotonate linked to chiral oxazolidones XP002712603, retrieved from STN Database accession No. 1993:408719 the abstract;and, in particular, the compounds with the Registry-Nos. [96727-96-7] and [148028-20-0] & Le Coz, Sylvie et al: 'Conjugate addition of organocuprates to methyl crotonate linked to chiral oxazolidones', Synthetic Communications, 23(2), 165-71 CODEN: SYNCAV; ISSN: 0039-7911, 1993.
CAS Registry Database, 1995:945500,Kadushkin, A. V. et al: 'Synthesis and neurotropic properties of oxazolidone analogs of piracetam', XP002712602, retrieved from STN Database accession No. 1995:945500 the abstract; and, in particular, the compound with the Registry-No. [172514-87-3] & Kadushkin, A. V. et al: 'Synthesi sand neurotropic properties of oxazolidone analogs of piracetam', Khimiko-Farmatsevticheskii 1Hurnal , 29(9), 20-2 CODEN: KHF1AN; ISSN: 0023-1134, 1995.
CAS Registry Database, 1997:594709,Shibata, Tomoyuki et al: 'Preparation and formulation of hydroxamic acid derivatives as matrix metalloproteinase inhibitors', XP002712601, retrieved from STN Database accession No. 1997:594709 the abstract; and, in particular, the compound with the Registry-No. [195510-34-0] & WO 97/31892 A1 (Sankyo Co., Ltd., Japan) Sep. 4, 1997 (Sep. 4, 1997).
CAS Registry Database, 2010:1115040,Chopin, Nathalie et al: 'Synthesis of the azetidinyl-thiazoline fragment of vioprolides A and C', XP002712599, retrieved from STN Database accession No. 2010:1115040 the abstract; and, in particular, the compound with the Registry-No. [1240490-38-3] & Chopin, Nathalie et al: 'Synthesis of the azetidinyl-thiazoline fragment of vioprolides A and C', Letters in Organic Chemistry, 7(5), 353-359 CODEN: LOCEC7; ISSN: 1570-1786, 2010.

(Continued)

*Primary Examiner* — Valerie Rodriguez-Garcia
(74) *Attorney, Agent, or Firm* — Robert C. Hall

(57) ABSTRACT

The invention provides compounds having the general formula I

I wherein n, $R^1$, $R^{2a}$, $R^{2b}$, $R^{3a}$ and $R^{3b}$ are as herein defined, composition comprising the compounds and methods of using the compounds.

21 Claims, No Drawings

(56) References Cited

OTHER PUBLICATIONS

Correa et al., "Guidelines for the evaluation of Pharmaceutical Patents" WHO, ICTSD and UNCTAD (Mar. 2008).
Dastlik et al., "An Expedient Route to the Glycine Templates (R)- or (S)-N-Cbz-5-Phenyl-1,4-oxazin-2-one" Tetrahedron 7(9):2525-2526 (Sep. 1996).
Hougaard et al., "A Positive Modulator of KCa2 and KCa3 Channels, 4,5-Dichloro-1,3-diethyl-1,3-dihydro-benzoimidazol-2-one (NS4591), Inhibits Bladder Afferent Firing in Vitro and Bladder Overactivity in Vivo" The Journal of Pharmacology and Experimental Therapeutics 328(1):28-39.
ISR for PCT/EP2013/072361.
Magee et al., "Diastereoselective [4+3] cycloaddition of enantiopure nitrogen-stabilized oxyallyl cations" Eur J of Org Chem 16:3667-3680 (Aug. 2006).
Matsui et al., "Application of erythro-2-amino-1,2-diphenylethanol as a highly efficient chiral auxiliary. Highly stereoselective Staudinger-type .beta.-lactam synthesis using a 2-chloro-1-methylpyridinium salt as the dehydrating agent" Synthesiis 8:1161-1166 (Aug. 1998).
Romine et al., "3-[(5-Chloro-2-hydroxyphenyl)methyl]-5-[4-(trifluoromethyl)phenyl]-1,3,4-oxadiazol-2(3H)-one, BMS-191011: Opener of Large-Conductance Ca2+-Activated Potassium (Maxi-K) Channels, Identification, Solubility, and SAR" J. Med. Chem. 50:528-242 (2007).
Takahashi et al., "Stereoselective reduction of (S)-4-isopropyl-3-phenacyl-1,3-oxazolidin-2-one by means of 1,4-asymmetric induction: synthesis of chiral 2-amino-1-phenylethanols" Chemical & Pharmaceutical 33(1):84-89 (1985).
Written Opinion for PCT/EP2013/072361.

\* cited by examiner

OXAZOLIDINONE AND IMIDAZOLIDINONE COMPOUNDS

The present invention relates to organic compounds useful for therapy or prophylaxis in a mammal, and in particular to KCa3.1 inhibitors, a channel implicated in a variety of secretion and cellular signaling events and are thus suitable for example for the treatment or prophylaxis of polycystic kidney disease.

The compounds of formula (I) are blockers of KCa3.1 (intermediate calcium activated potassium channel, otherwise known as KCCN4, IK1, IKCA1, KCA4, SK4, hIKCa1, hKCa4, hSK4 and the Gardos channel).

KCa3.1 channels are found in hematopoietic-derived cells (i.e. erythrocytes, platelets, lymphocytes, mast cells and monocytes/macrophages), epithelial tissues in the gastrointestinal tract, lung and endo- and exocrine glands; as well as vascular endothelial cells, fibroblasts and proliferating neointimal vascular smooth muscle cells. (H. Wulff Expert Rev. Clin. Pharmacol. 2010, 3, 385).

For the KCa3.1 channel expressed in the epithelium lining of the gastrointestinal tract, in lung epithelia, in ducts of fluid-secreting glands (i.e. salivary, lacrimal, pancreas and prostate), as well as in stratified epithelia (including skin, the cornea, oral mucosa and urothelium) activation of KCa3.1 channels provides a pathway for potassium flux which helps to facilitate chloride secretion and consequently water transport across the epithelia. This is of particular relevance for the treatment of polycystic kidney disease (PKD), more particularly autosomal dominant polycystic kidney disease (ADPKD), where cAMP-dependent chloride secretion is believed to be a key driver of cyst enlargement and disease progression. It has been shown in MDCK 3-D cyst model of ADPKD, that application of the KCa3.1 blocker TRAM-34, inhibits cyst formation (M. Albaqumi et al. Kidney International 2008, 74, 740).

The loss of potassium ions via the KCa3.1 channel from the cell also contributes to the maintenance of a negative membrane potential, helping to sustain calcium entry into cells. Elevation of intracellular $Ca^{2+}$ is necessary for the production of inflammatory chemokines and cytokines by T-cells, macrophages and mast cells. It is also a prerequisite for the proliferation of many cell types. KCa3.1-mediated control of Ca2+ entry has further been shown to be involved in the migration of macrophages (I. Chung et al. J. Neuroimmunol. 2002, 122, 40), microglia (T. Schilling et al. Eur. J. Neurosci. 2004, 19, 1496), vascular smooth muscle cells (D. Tharp et al. Am. J. Physiol. Heart Circ. Physiol. 2006, 291, H2493) and mast cells (G. Cruse et al. Thorax 2006, 61, 880).

The anti-inflammatory effects of KCa3.1 blockade have been demonstrated both in animal models of rheumatoid arthritis (C Chou in IBC Assays and Celluclar Targets 2005 (CA, USA) and in humans (J. Wojtulewski et al Ann. Rheum. Dis. 1980, 39, 469). The KCa3.1 blocker Senicapoc has been shown to reduce allergen challenge-induced airway resistance and hyper-reactivity in a sheep model of asthma (US2010/0056637A1). KCa3.1 blockers have also been shown to be neuroprotective, reducing brain edema and infarct volume of traumatic brain injury in rats (F. Mauler et al. Eur. J. Neurosci. 2004, 20, 1761). Treatment of mice with KCa3.1 blocker TRAM-34 in a model of human inflammatory bowel disease (trinitrobenzene sulfonic acid-induced colitis) significantly reduced the severity of the symptoms. (Proc. Natl. Acad. Sci. USA 2010, 107, 1541). It has also been shown that the KCa3.1 blocker TRAM-34 in combination with a Kv1.3 blocker reduced T-cell and macrophage infiltration during the early stages of chronic kidney transplant rejection (I. Grgic Transplant. Proc. 2009, 41, 2601).

The anti-proliferative effects of KCa3.1 blockade have been demonstrated in numerous different animal models. For example, treatment of rats that have undergone carotid balloon angioplasty with TRAM-34 had significantly reduced neointimal smooth muscle hyperplasia (R. Kohler et al. Circulation 2003, 108, 1119) and similarly in the porcine coronary overstretch model in pigs (D. Tharp Thromb. Vasc. Biol. 2008, 28, 1084) which is of particular relevance for the treatment of restenosis. KCa3.1 blockade in ApoE$^{-/-}$ mice significantly reduced the development of atherosclerosis by reducing smooth muscle cell proliferation (K. Toyama et al. J. Clin. Invest. 2008, 118, 3025). In the unilateral ureteral obstruction model, it has been shown that treatment with KCa3.1 blocker TRAM-34 significantly reduced renal fibrosis by preventing fibroblast proliferation (I. Grgic Proc. Natl. Acad. Sci. USA 2009, 106, 14518).

KCa3.1 blockade has also been shown to play a role in the development of various forms of cancer, being involved in the proliferation of human LNCaP and PC-3 prostrate cancer cells, leukemic HL-60 and glioblastoma G1-15 cells, MCF-7 breast cancer cell, BxPC-3 and MIaPa Ca-2 pancreatic cancer cells and HEC-1a and KLE endometrial cancer cells (C. Chou et al. Expert. Rev. Mol. Diagn. 2008, 8, 179). KCa3.1 blocker Clotrimazole has been shown to both reduce the number of metastases in severe combined immunodeficiency mice innocluated with human melanoma (L. Benzaquen Nat. Med. 1995, 1, 534) and slowed the growth of tumours in nude mice injected with human endometrial cancer cells (Z. Wang et al. Oncogene 2007, 26, 5107).

The invention is concerned with novel compounds of formula I,

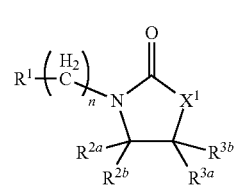

wherein
$X^1$ is O or NH;
n is an integer between 1 to 4;
$R^1$ is hydrogen, cyano, —C(O)$R^{1a}$, —C(O)NR$^{1b}$R$^{1c}$, heteroaryl or CH$_2$OH;
$R^{1a}$ is hydrogen, $C_1$-$C_6$ alkyl, $C_1$-$C_6$ alkoxy, phenyl or heteoaryl;
$R^{1b}$ and $R^{1c}$ are each independently hydrogen, $C_1$-$C_6$ alkyl, phenyl or heteoaryl, wherein said $C_1$-$C_6$ alkyl, said phenyl or said heteoaryl are optionally substituted with one or more, particularly one to three substituents independently selected from the group consisting of hydroxy, halogen, $C_1$-$C_6$ alkyl, $C_1$-$C_6$ alkoxy, haloC$_1$-$C_6$ alkyl and haloC$_1$-$C_6$ alkoxy;
$R^{2a}$ is hydrogen or $C_1$-$C_6$ alkyl;
$R^{2b}$ is haloC$_1$-$C_6$alkyl, $C_1$-$C_6$ alkyl, phenyl or heteroaryl, wherein said phenyl or said heteroaryl are optionally substituted with one or more, particularly with one or two substituents independently selected from the group consisting of hydroxy, halogen, $C_1$-C alkyl and haloC$_1$-$C_6$alkyl;
$R^{3a}$ and $R^{3b}$ are each independently hydrogen, phenyl or heteroaryl, wherein said phenyl or said heteoaryl are optionally substituted with one or more, particularly one to three substituents independently selected from the group consisting of halogen, $C_1$-$C_6$alkyl and halo$C_1$-$C_6$alkyl;

or pharmaceutically acceptable salts.

The application provides a method for treating polycystic kidney disease comprising administering to a patient in need thereof a therapeutically effective amount of the compound of Formula I, I' or I".

Further, the invention is concerned with a process for the manufacture of the above compounds, pharmaceutical preparations which contain such compounds, the use of these compounds for the production of pharmaceutical preparations.

Unless otherwise stated, the following terms used in the specification and claims have the meanings given below:

"halo" or "halogen" means fluoro, chloro, bromo or iodo, particularly chloro or fluoro, more particularly fluoro.

"hydroxy" refers to a —OH group.

"($C_1$-$C_6$)alkyl" refers to a branched or straight hydrocarbon chain of one to six carbon atoms, such as methyl, ethyl, n-propyl, isopropyl, n-butyl, isobutyl, sec-butyl, t-butyl, pentyl and hexyl.

"($C_1$-$C_6$)alkoxy" means a moiety of the formula —$OR^a$, wherein $R^a$ is an ($C_1$-$C_6$)alkyl moiety as defined herein. Examples of ($C_1$-$C_6$)alkoxy moieties include, but are not limited to, methoxy, ethoxy, isopropoxy, and the like.

The term "perhalo($C_1$-$C_3$)alkyl" means an ($C_1$-$C_3$)alkyl group as defined above wherein all hydrogen atoms have been replaced with halogen atoms. More particularly "($C_1$-$C_3$)perhaloalkyl" is ($C_1$-$C_3$)perfluoroalkyl, most preferably trifluoromethyl.

"halo-($C_1$-$C_6$)alkyl" refers to an alkyl, as defined above, substituted with one or more halogen atoms, particularly with one to three halogen atoms. More particularly halo-($C_1$-$C_6$)alkyl is the chloro- and fluoro-($C_1$-$C_6$)alkyl. In some particular embodiment halo-($C_1$-$C_6$)alkyl refers to perhalo ($C_1$-$C_3$)alkyl, such as trifluoromethyl.

"halo-($C_1$-$C_6$)alkoxy" refers to an alkoxy, as defined above, substituted with one or more halogen atoms, particularly with one to three halogen atoms. More particularly halo-($C_1$-$C_6$)alkoxy are the chloro- and fluoro-($C_1$-$C_6$) alkoxy.

"Heteroaryl" means a monovalent monocyclic or bicyclic moiety of 5 to 12 ring atoms having at least one aromatic ring containing one, two, or three ring heteroatoms selected from N, O, or S (preferably N or O), the remaining ring atoms being C, with the understanding that the attachment point of the heteroaryl moiety will be on an aromatic ring. More specifically the term heteroaryl includes, but is not limited to, pyridinyl, furanyl, thienyl, thiazolyl, isothiazolyl, triazolyl, imidazolyl, isoxazolyl, oxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof. Most particularly "heteroaryl" refers to pyridinyl, oxazolyl or triazolyl (more particularly 1,2,4-triazolyl).

"Optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The term "independently" is used herein to indicate that a variable is applied in any one instance without regard to the presence or absence of a variable having that same or a different definition within the same compound.

Particularly, for the terms which definitions are given above are those specifically exemplified in the examples.

Compounds that have the same molecular Formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula (I) can possess one or more asymmetric centers. Unless indicated otherwise, the description or naming of a particular compound in the specification and claims is intended to include both individual enantiomers and mixtures, racemic or otherwise, thereof, as well as individual epimers and mixture thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

Certain compounds may exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

In another embodiment, the invention provides a compound of formula I'

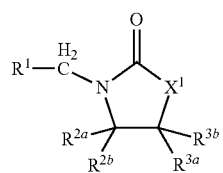

wherein $R^1$, $R^{2a}$, $R^{2b}$, $R^{3a}$ and $R^{2b}$ are as herein defined.

In another embodiment, the invention provides a compound of formula I"

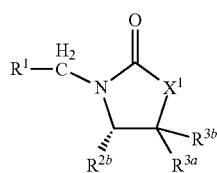

wherein $R^1$, $R^{2a}$, $R^{2b}$, $R^{3a}$ and $R^{3b}$ are as herein defined.

In particular embodiment, the present invention provides a compound of formula I, I' or I" as described herein, wherein $X^1$ is O.

In particular embodiment, the present invention provides a compound of formula I as described herein, wherein n is 1 or 2, more particularly wherein n is 1.

In particular embodiments, the present invention provides a compound of formula I, I' or I" as described herein, wherein $R^1$ is hydrogen, cyano, —C(O)$R^{1a}$, —C(O)NR$^{1b}$R$^{1c}$ or heteroaryl, particularly $R^1$ is hydrogen, cyano, —C(O)$R^{1a}$, —C(O)NR$^{1b}$R$^{1c}$ or triazolyl (more particularly 1,2,4-triazolyl), more particularly wherein $R^1$ is cyano, —C(O)$R^{1a}$, —C(O)NR$^{1b}$R$^{1c}$ or triazolyl (more particularly 1,2,4-triazolyl), even more particularly wherein $R^1$ is cyano, —C(O)$R^{1a}$ or —C(O)NR$^{1b}$R$^{1c}$, most particularly wherein $R^1$ is —C(O)$R^{1a}$ or —C(O)NR$^{1b}$R$^{1c}$.

In particular embodiments, the present invention provides a compound of formula I, I' or I" as described herein, wherein $R^{1a}$ is hydrogen, $C_1$-$C_3$ alkyl, $C_1$-$C_3$ alkoxy, more particular wherein $R^{1a}$ is $C_1$-$C_3$ alkoxy, most particularly wherein $R^{1a}$ is methoxy or ethoxy.

In particular embodiments, the present invention provides a compound of formula I, I' or I" as described herein, wherein $R^{1b}$ and $R^{1c}$ are each independently hydrogen, $C_1$-$C_3$ alkyl, phenyl or heteroaryl, more particular wherein $R^{1b}$ and $R^{1c}$ are each independently hydrogen or $C_1$-$C_3$ alkyl, most particular wherein $R^{1b}$ and $R^{1c}$ are each independently hydrogen, methyl or ethyl.

In particular embodiments, the present invention provides a compound of formula I or I' as described herein, wherein $R^{2a}$ is hydrogen.

In particular embodiments, the present invention provides a compound of formula I or I' as described herein, wherein $R^{2b}$ is perhalo$C_1$-$C_3$alkyl, $C_1$-$C_3$ alkyl, phenyl or heteroaryl, wherein said phenyl or said heteroaryl are optionally substituted with one or more, particularly with one or two substituents independently selected from the group consisting of hydroxy, halogen, $C_1$-$C_3$ alkyl and halo$C_1$-$C_3$alkyl.

In another particular embodiments, the present invention provides a compound of formula I, I' or I" as described herein, wherein $R^{2b}$ is perhalo$C_1$-$C_3$alkyl, $C_1$-$C_3$ alkyl, phenyl or pyridinyl, wherein said phenyl or said pyridinyl are optionally substituted with one or two substituents independently selected from the group consisting of halogen, $C_1$-$C_3$ alkyl and halo$C_1$-$C_3$alkyl, in particular wherein $R^{2b}$ is phenyl or pyridinyl, wherein said phenyl or said pyridinyl are optionally substituted with one or two substituents independently selected from the group consisting of halogen and $C_1$-$C_3$ alkyl.

In particular embodiments, the present invention provides a compound of formula I, I' or I" as described herein, wherein $R^{2b}$ is phenyl optionally substituted with one or two substituents independently selected from the group consisting of halogen and $C_1$-$C_3$ alkyl.

In particular embodiments, the present invention provides a compound of formula I, I' or I" as described herein, wherein $R^{2b}$ is phenyl optionally substituted with one or two substituents independently selected from the group consisting of chloro, fluoro and methyl.

In particular embodiments, the present invention provides a compound of formula I, I' or I" as described herein, wherein $R^{3a}$ and $R^{3b}$ are each independently phenyl optionally substituted with one or more, particularly one to two halogen, in particular wherein $R^{3a}$ and $R^{3b}$ are each independently phenyl optionally substituted with one to two chloro or fluoro.

In particular embodiments, the present invention provides a compound of formula I, I' or I" as described herein, wherein $R^{3a}$ and $R^{3b}$ are the same and are phenyl optionally substituted with one or more, particularly one to two chloro or fluoro, more particularly wherein both $R^{3a}$ and $R^{3b}$ are phenyl substituted with one fluoro, most particularly wherein both $R^{3a}$ and $R^{3b}$ are phenyl para substituted with one fluoro.

In a more particular embodiment, the present invention provides a compound of formula I, I' or II" as described herein, wherein $X^1$ is O, $R^1$ is —C(O)NR$^{1b}$R$^{1c}$, wherein wherein R$^{1b}$ and R$^{1c}$ are each independently hydrogen, $C_1$-$C_3$ alkyl, phenyl or heteroaryl, R$^{2a}$ is hydrogen, R$^{2b}$ is perhaloC$_1$-C$_3$alkyl, $C_1$-$C_3$ alkyl, phenyl or pyridinyl, wherein said phenyl or said pyridinyl are optionally substituted with one or two substituents independently selected from the group consisting of halogen, $C_1$-$C_3$ alkyl and haloC$_1$-C$_3$alkyl, R$^{3a}$ and R$^{3b}$ are each independently phenyl optionally substituted with one or more, particularly one to two halogen.

More particularly, the present invention provides a compound of formula I, I' or II" as described herein, wherein $X^1$ is O, $R^1$ is —C(O)NR$^{1b}$R$^{1c}$, wherein R$^{1b}$ and R$^{1c}$ are hydrogen, wherein R$^{2a}$ is hydrogen, R$^{2b}$ is phenyl optionally substituted with one or two substituents independently selected from the group consisting of chloro, fluoro and methyl, wherein R$^{3a}$ and R$^{3b}$ are each independently phenyl optionally substituted with one or more particularly one to two halogen.

More particularly, the present invention provides a compound of formula I, I' or II" as described herein, wherein $X^1$ is O, $R^1$ is —C(O)NR$^{1b}$R$^{1c}$, wherein R$^{1b}$ and R$^{1c}$ are hydrogen, wherein R$^{2a}$ is hydrogen, R$^{2b}$ is phenyl optionally substituted with one or two substituents independently selected from the group consisting of chloro, fluoro and methyl, wherein R$^{3a}$ and R$^{3b}$ are phenyl substituted with one fluoro.

More particularly, the present invention provides a compound of formula I, I' or II" as described herein, wherein $X^1$ is O, $R^1$ is —C(O)NR$^{1b}$R$^{1c}$, wherein R$^{1b}$ and R$^{1c}$ are hydrogen, wherein R$^{2a}$ is hydrogen, R$^{2b}$ is phenyl optionally substituted with one or two substituents independently selected from the group consisting of chloro, fluoro and methyl, wherein R$^{3a}$ and R$^{3b}$ are phenyl para substituted with fluoro.

Particular examples of compounds of formula (I) as described herein are selected from:
2-[(S)-4-(2,4-Difluoro-phenyl)-5,5-bis-(4-fluoro-phenyl)-2-oxo-oxazolidin-3-yl]-acetamide;
2-[(S)-4,5,5-Tris-(4-fluoro-phenyl)-2-oxo-oxazolidin-3-yl]-acetamide;
2-[(S)-5,5-Bis-(4-fluoro-phenyl)-4-(2-fluoro-phenyl)-2-oxo-oxazolidin-3-yl]-acetamide;
2-[(S)-4,5,5-Tris-(2-fluoro-phenyl)-2-oxo-oxazolidin-3-yl]-acetamide;
2-[(S)-5,5-Bis-(3-fluoro-phenyl)-4-(2-fluoro-phenyl)-2-oxo-oxazolidin-3-yl]-acetamide;
2-[(S)-4-(2-Fluoro-phenyl)-2-oxo-5,5-diphenyl-oxazolidin-3-yl]-acetamide;
2-[(S)-4-(2-Chloro-phenyl)-5,5-bis-(4-fluoro-phenyl)-2-oxo-oxazolidin-3-yl]-acetamide;
(S)-methyl 2-(4-(2-fluorophenyl)-5,5-bis(4-fluorophenyl)-2-oxooxazolidin-3-yl)acetate;
(S)-2-(4-(2-fluorophenyl)-5,5-bis(4-fluorophenyl)-2-oxooxazolidin-3-yl)-N-methylacetamide;
(S)-2-(5,5-bis(3,4-difluorophenyl)-2-oxo-4-phenyloxazolidin-3-yl)acetamide;
and pharmaceutically acceptable salts thereof.

In another embodiment, the present invention provides a compound according to formula I, I' or I" as described herein for use as a therapeutically active substance.

In yet another embodiment, the present invention provides a compound according to formula I, I' or I" as described herein for the treatment or prophylaxis of polycystic kidney disease, asthma, brain edema, inflammatory bowel disease, transplant rejection, atherosclerosis, renal fibrosis, cancer, restenosis.

In particular embodiment, the present invention provides a compound according to formula I, I' or I" as described herein for the treatment or prophylaxis of polycystic kidney disease.

According to the invention, cancer refers in particular to melanoma, leukemia, breast, pancreatic and endometrial cancers.

In another embodiment, the present invention provides the use of a compound according to formula I, I' or I" as described herein for the preparation of a medicament for the treatment or prophylaxis of polycystic kidney disease, asthma, brain edema, inflammatory bowel disease, transplant rejection, atherosclerosis, renal fibrosis, cancer. restenosis.

In one aspect, the application provides a method of treating a KCa3.1 disorder in a subject having KCa3.1 related disorders, said method comprising administering to a subject in need thereof a therapeutically effective amount of any of the above compounds.

In another embodiment, the present invention provides a method of treatment or prophylaxis of polycystic kidney disease, asthma, brain edema, inflammatory bowel disease, transplant rejection, atherosclerosis, renal fibrosis, cancer, restenosis, which comprises administering an effective amount of a compound according to formula I, I' or I" as described herein.

In particular embodiment, the present invention provides a method of treatment or prophylaxis of polycystic kidney disease, which comprises administering an effective amount of a compound according to formula I, I' or I" as described herein.

In particular KCa3.1 disorders or KCa3.1 related diseases are polycystic kidney disease, asthma, brain edema, inflammatory bowel disease, transplant rejection, atherosclerosis, renal fibrosis, cancer, restenosis.

In one aspect, the application provides a pharmaceutical composition comprising the compound of any one of the above embodiments, admixed with at least one pharmaceutically acceptable carrier, such as excipient or diluent.

In another embodiment, the present invention provides a use of a compound of Formula I, I' or I" in the preparation of a medicament for the treatment of diseases associated with KCa3.1.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. For example, such amount may be below the amount that is toxic to normal cells, or the mammal as a whole.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and pharmaceutically acceptable carrier or excipient. Suitable pharmaceutically acceptable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

An embodiment, therefore, includes a pharmaceutical composition comprising a compound according to the invention herein described, or a stereoisomer thereof. In a further embodiment includes a pharmaceutical composition comprising a compound according to the invention herein described, or a stereoisomer thereof, together with a pharmaceutically acceptable carrier or excipient.

Another embodiment includes a pharmaceutical composition comprising a compound according to the invention herein described for use in the treatment of a KCa3.1 related diseases. Another embodiment includes a pharmaceutical composition comprising a compound according to the invention herein described for use in the treatment of KCa3.1 related diseases.

In another embodiment the present invention provides the manufacture of compounds of formula (I) as described herein.

The preparation of compounds of formula (I) of the present invention may be carried out in sequential or convergent synthetic routes. Syntheses of the invention are shown in the following general scheme. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization.

Furthermore the compounds of the present invention can be prepared from commercially available starting materials or by the use of general synthetic techniques and procedures that are known to those skilled in the art. Outlined below is a reaction scheme 1 suitable for the preparation of such compounds. The substituents and indices used in the following description of the processes have the significance given herein. Further exemplification can be found in the specific examples detailed below.

Scheme 1

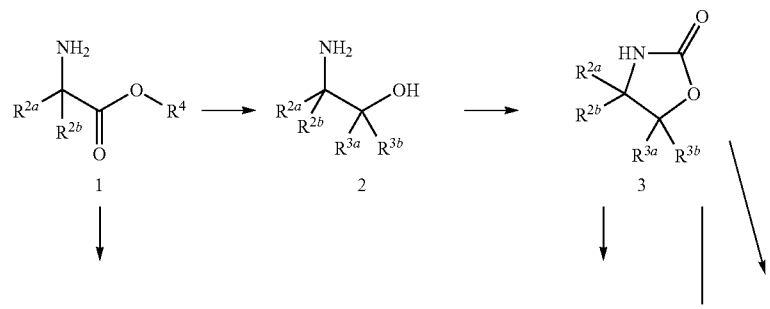

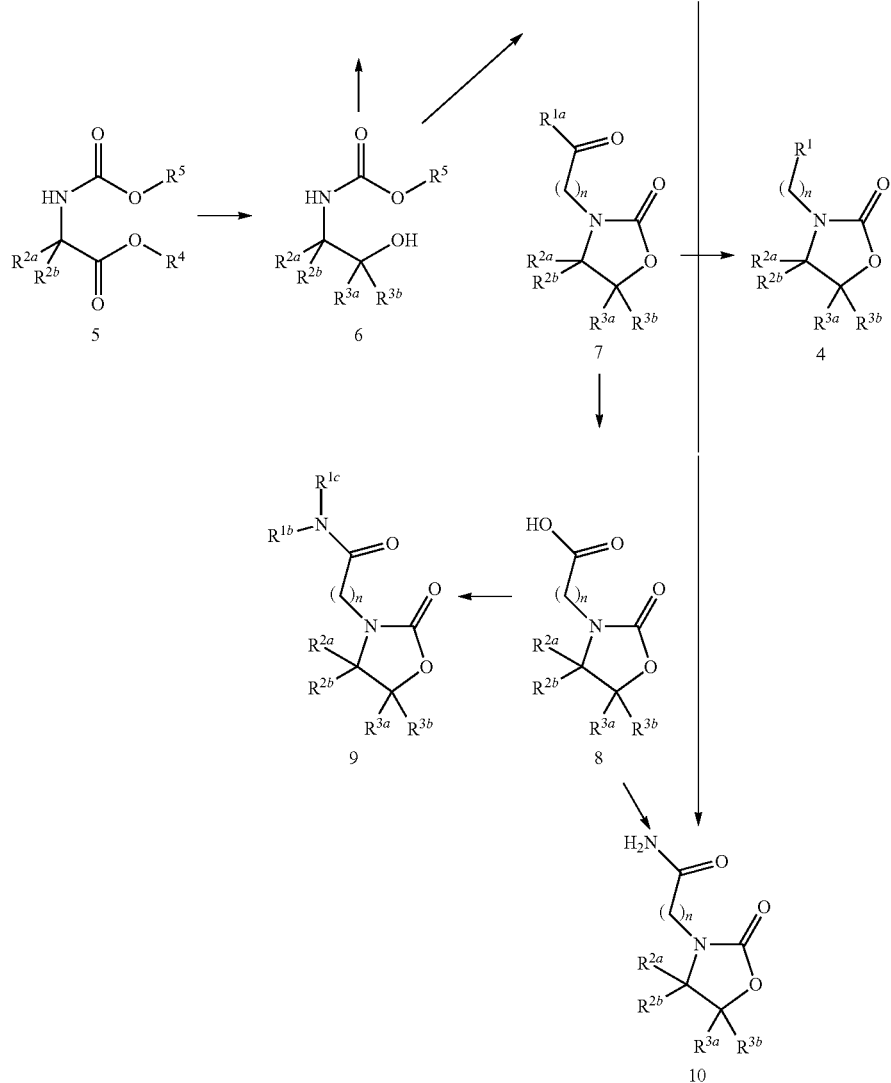

In Scheme $R^1$, $R^{1a}$, $R^{1b}$, $R^{2a}$, $R^{2b}$, $R^{3a}$, $R^{3b}$, $R^4$ and $R^5$ are as defined herein.

General Synthetic Procedures

Esters 1 are commercially available or can be readily prepared from commercially available aminoacids by known methods ($R^4$ is typically ($C_1$-$C_6$) alkyl e.g. methyl or ethyl). Direct reaction of 1 with an excess of Grignard reagents (either commercially available or prepared from the corresponding halide using known methods e.g. treatment with magnesium metal in refluxing THF or by an exchange reaction with isopropylmagnesium choride lithium chloride complex in THF at reduced temperatures e.g. 0-10° C.). installs groups $R^{3a}R^{3b}$ affording aminoalcohol 2. Subsequent cyclisation of 2 to the oxazolidinone 3 can be performed by use of a phosgene or phosgene equivalent (e.g. diphosgene, triphosgene) in the presence of an amine base (e.g. triethylamine) in a solvent such as dichloromethane at reduced temperatures (0° C. or lower), or by using 1,1'-carbonyldiimidazole in the same solvent. Alternatively, 3 wherein $R^5$=$C_1$-$C_6$ alkyl, can be prepared by first protecting the amine functionality of 1 with a carbamate protecting group e.g. tert-butoxycarbonyl, ethoxycarbonyl by known methods to afford 5 and subsequent reaction with an excess of Grignard reagent to afford protected amino-alcohol 6. In the case that $R^5$=tert-butyl, acidic deprotection (e.g. 4 N hydrochloric acid in dioxane, or trifluoracetic acid, either pure or in dichloromethane solution) leads to compound 2. In the case that $R^5$ is a lower alkyl e.g. methyl or ethyl then treatment of 6 with stoichiometric amount of a strong base e.g. potassium tert-butylate in a polar solvent such as ethanol at room temperature or with heating e.g. 80° C., leads directly to oxazolidinone 3. Oxazolidinone 3 can then be derivatised by deprotonation and subsequent reaction with an alkylating group. For example, it can be reacted with heteroaryl alkyhalides by deprotonation with strong bases (e.g. sodium hydride) in solvents such as THF or DMF at ambient or reduced temperature e.g 0° C. to afford products 4, or alternatively reacted with haloakylacetate derivatives under identical conditions to afford ester 7 (where $R^{1a}$ is ($C_1$-$C_6$)alkoxy e.g. methoxy or ethoxy). This ester can then be converted to heterocycle 4 using known methods. Ester 7 can then be saponified under standard conditions (e.g. treatment with aqueous sodium hydroxide in alcoholic solvents such as ethanol, methanol) to afford carboxylic acid 7. Activation of this acid using standard reagents (e.g. 1,1-carbonyldimidazole, 2-(1H-benzotriazolel-yl)-1,1,3,3-tetramethyluronomium tetrafluoroborate) in polar solvents such as DMF, and reaction with amines affords product 9 wherein $R^{1b}$ and $R^{1c}$ are as defined herein, or reaction with ammonia affords product 10. Alternatively product 10 can be prepared directly from oxazolidinone 3 by deprotonation of 3 with strong bases (e.g. sodium hydride) in solvents such as THF or DMF at ambient or reduced temperature e.g 0° C. and alkylation with for example, 2-bromoacetamide for the case of n=1. In the event that $R^{3a}$ and $R^{3b}$ are not the same an alternative approach is required (scheme 2). Protected aminoacids 11 wherein $R^5$ is as described herein can be converted to the corresponding N-methoxy, N-methyl amides 12 by conventional amide coupling methods. Reaction of 12 with excess Grignard reagent (as described herein) affords ketone 13. This ketone can subsequently be reacted with a different Grignard reagent to afford aminoalcohol 6 where $R^{3a}$ and $R^{3b}$ are not the same as described herein. For the case where $R^{3b}$=H, ketone 13 can be selectively reduced to the cis-alcohol with sodium borohydride in methanol. Aminoalcohol 6 can subsequently be elaborated to end-products in the manner described by Scheme 1.

Scheme 3. General synthesis of imidazolinone derivatives

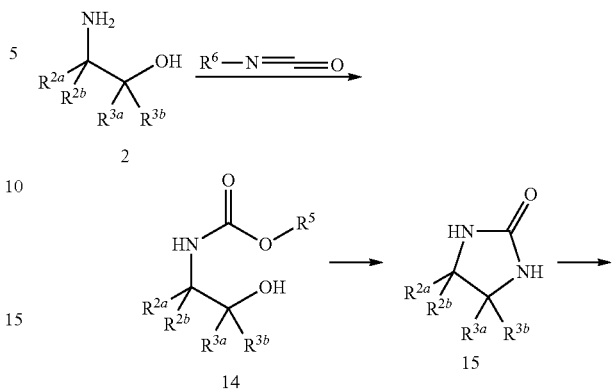

In Scheme 3, $R^{2a}$, $R^{2b}$, $R^{3a}$, $R^{3b}$ and $R^6$ are as defined herein.

The following Examples serve to illustrate the present invention in more detail. They are, however, not intended to limit its scope in any manner. All reactions are performed under inert atmosphere unless otherwise specified.

In general, the nomenclature used in this Application is based on Struct2Name, a Perkin Elmer computerized system for the generation of IUPAC systematic nomenclature. If there is a discrepancy between a depicted structure and a name given that structure, the depicted structure is to be Scheme 2. General synthesis of usymmetrically $R^{3a}/R^{3b}$ substituted derivatives.

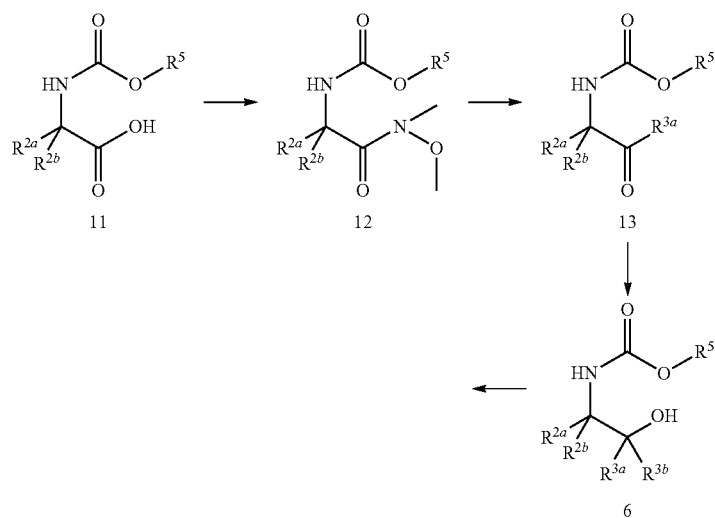

In Scheme 2, $R^{2a}$, $R^{2b}$, $R^{3a}$, $R^{3b}$, and $R^5$ are as defined herein.

The synthesis of imidazolinone derivatives starts from aminoalcohol 2 (Scheme 1) which is then reacted with an isocyanate bearing an acid labile group $R^6$, e.g. 4-methoxybenzyl, in an inert solvent such as tetrahyrdofuran or dichloromethane, affording urea 14. This compound can be simultaneously cyclised and deprotected by heating with a Lewis acid such as boron trifluoride etherate in an inert solvent e.g. dichloromethane affording imidazolinone 15. This intermediate can then be elaborated in the same manner as 3 (Scheme 1).

accorded more weight. In addition, if the stereochemistry of a structure or a portion of a structure is not indicated with, for example, bold or dashed lines, the structure or portion of the structure is to be interpreted as encompassing all stereoisomers of it.

ABBREVIATIONS

DMF dimethylformamide
EtOAc ethyl acetate
n-Hept n-heptane
HPLC high-pressure liquid chromatography MS mass spectrometry
THF tetrahydrofuran

EXAMPLE 1

(S)-2-(5,5-bis(4-fluorophenyl)-2-oxo-4-phenyloxazolidin-3-yl)acetamide

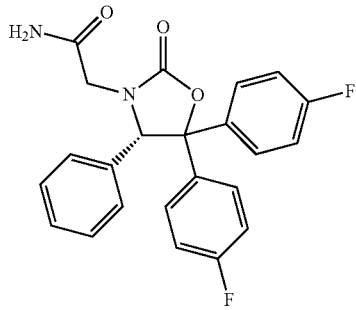

A) (S)-2-amino-1,1-bis(4-fluorophenyl)-2-phenylethanol

To an ice-cold suspension of (S)-methyl 2-amino-2-phenylacetate hydrochloride (1 g, 5.0 mmol) in THF (50 ml) is added dropwise (4-fluorophenyl)magnesium bromide (19.8 ml, 1 M in THF, 20 mmol). On completion of the addition, the ice bath was removed and the reaction allowed to reach ambient temperature. The reaction was then poured onto saturated ammonium chloride solution and extracted with ethyl acetate. The combined organic layers were washed with brine, dried ($Na_2SO_4$) and concentrated. Purification by flash column chromatography (eluent EtOAc:n-Hept gradient 1:4-1:1) afforded the title compound as a colourless, crystalline solid (0.8 g, 50%). MS: $(MH)^+$ 326.2.

B) (S)-5,5-bis(4-fluorophenyl)-4-phenyloxazolidin-2-one

To an ice-cold solution of (S)-2-amino-1,1-bis(4-fluorophenyl)-2-phenylethanol (0.8 g, 2.5 mmol) and triethylamine (1.0 ml, 7.5 mmol) in methylene chloride (15 ml) was added a solution of trichloromethyl chloroformate (0.3 ml, 2.5 mmol) in methylene chloride (2 ml). The ice bath was removed and the reaction allowed to reach ambient temperature. The reaction was then diluted with methylene chloride, washed with 1N hydrochloric acid, dried ($Na_2SO_4$) and concentrated. Purification by flash column chromatography (eluent EtOAc:n-Hept gradient 1:4-3:2) afforded the title compound as a colourless, crystalline solid (0.7 g, 80%). MS: $(MH)^+$ 352.2.

C) (S)-ethyl 2-(5,5-bis(4-fluorophenyl)-2-oxo-4-phenyloxazolidin-3-yl)acetate To an ice-cold solution of (S)-5,5-bis(4-fluorophenyl)-4-phenyloxazolidin-2-one (0.2 g, 0.6 mmol) and ethyl 2-bromoacetate (76 µl, 0.7 mmol) in THF (5 ml) was added sodium hydride (0.05 g, 60% dispersion in mineral oil, 1.1 mmol). The ice bath was removed and the reaction allowed to reach ambient temperature. The reaction was then diluted with methylene chloride, washed with 1N hydrochloric acid, dried ($Na_2SO_4$) and concentrated. Purification by flash column chromatography (eluent EtOAc: n-Hept 2:3) afforded the title compound as an off-white, crystalline solid (0.25 g, 84%). MS: $(MH)^+$ 438.2.

D) (S)-2-(5,5-bis(4-fluorophenyl)-2-oxo-4-phenyloxazolidin-3-yl)acetic acid

To a suspension of (S)-ethyl 2-(5,5-bis(4-fluorophenyl)-2-oxo-4-phenyloxazolidin-3-yl)acetate (0.19 g, 0.4 mmol) in ethanol (5 ml) was added sodium hydroxide (0.15 ml, 6 M in water, 0.9 mmol) and the reaction stirred for 15 minutes. The reaction was then acidified using Amberlite® IR120 resin, filtered and concentrated to afford the title compound (0.18 g, 100%) as a colourless foam. MS: $(M-H)^-$ 408.2.

E) (S)-2-(5,5-bis(4-fluorophenyl)-2-oxo-4-phenyloxazolidin-3-yl)acetamide

To a solution of (S)-2-(5,5-bis(4-fluorophenyl)-2-oxo-4-phenyloxazolidin-3-yl)acetic acid (0.12 g, 0.3 mmol) in DMF (1 ml) was added 1,1-carbonyldimidazole (61 mg, 0.3 mmol) and the mixture stirred for 1 h at 60° C. After cooling to ambient temperature ammonium hydroxide (0.5 ml, 25% in water, 3.1 mmol) was added and the mixture stirred for 2 h after which time it was concentrated to dryness. The residue was partitioned between water and ethyl acetate, the organic washed with brine dried ($Na_2SO_4$) and concentrated. Purification by flash column chromatography (eluent gradient EtOAc: n-Hept 0:1-1:0) afforded the title compound as a white foam (0.083 g, 65%). MS: $(MH)^+$ 409.3.

EXAMPLE 2

2-[(S)-5,5-Bis-(2-fluoro-phenyl)-2-oxo-4-phenyloxazolidin-3-yl]-acetamide

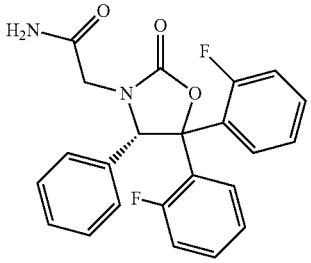 [SMILES: NC(=O)CN1C(=O)OC(c2ccccc2F)(c2ccccc2F)[C@@H]1c1ccccc1]

A) (S)-tert-butyl 2,2-bis(2-fluorophenyl)-2-hydroxy-1-phenylethylcarbamate

To isopropylmagnesium chloride-lithium chloride complex (38.5 ml, 1.3 M in THF, 50 mmol), cooled in a water bath, was added 1-fluoro-2-iodobenzene at a rate such that the temperature remained below 40° C. On completion of the addition the mixture was stirred for 0.5 h. It was then added to a solution of (S)-methyl 2-(tert-butoxycarbonylamino)-2-phenylacetate (3.8 g, 14.3 mmol) in THF (20 ml) with water bath cooling. The mixture was stirred for a further 3 h after which time it was poured onto saturated ammonium chloride solution and extracted with ethyl acetate. The combined organic layers were washed with brine, dried ($Na_2SO_4$) and concentrated. Purification by flash column chromatography (eluent EtOAc: n-Hept gradient 0:1-1:1) and subsequent recrystallization from EtOAc/n-hexane afforded the title compound as a colourless, crystalline solid (1.8 g, 30%). MS: (M–H)⁻ 424.3

B) (S)-2-amino-1,1-bis(2-fluorophenyl)-2-phenylethanol

To a solution of(S)-tert-butyl 2,2-bis(2-fluorophenyl)-2-hydroxy-1-phenylethylcarbamate (1.8 g, 4.2 mmol) in methylene chloride (25 ml) was added trifluoroacetic acid (3.6 ml, 46 mol) and the mixture stirred for 2 h at ambient temperature. The mixture was then cautiously poured onto saturated sodium hydrogen carbonate solution and the product extracted with methylene chloride. The combined organic layers were washed with brine, dried (Na₂SO₄) and concentrated to afford the title compound as a colourless, solid (1.4 g, 96%). MS: (MH)⁺ 326.1.

C) (S)-5,5-bis(2-fluorophenyl)-4-phenyloxazolidin-2-one

To an ice-cold solution (S)-2-amino-1,1-bis(2-fluorophenyl)-2-phenylethanol (0.3 g, 0.9 mmol) and triethylamine (0.4 ml, 2.8 mmol) in methylene chloride (6 ml) was added a solution of trichloromethyl chloroformate (0.06 ml, 0.5 mmol) in methylene chloride (2.5 ml). The ice bath was removed and the reaction allowed to come to ambient temperature.

The reaction was then diluted with methylene chloride, washed with 1N hydrochloric acid, brine, dried (Na₂SO₄) and concentrated. Purification by flash column chromatography (eluent EtOAc: n-Hept gradient 0:1-1:0) afforded the title compound as a colourless solid (0.2 g, 58%). MS: (MH)⁺ 352.2.

D) 2-[(S)-5,5-Bis-(2-fluoro-phenyl)-2-oxo-4-phenyl-oxazolidin-3-yl]-acetamide

The title compound was prepared from (S)-5,5-bis(2-fluorophenyl)-4-phenyloxazolidin-2-one in analogy to example 1 (steps C, D and E) as a white foam. MS: (MH)⁺ 409.3.

EXAMPLE 3

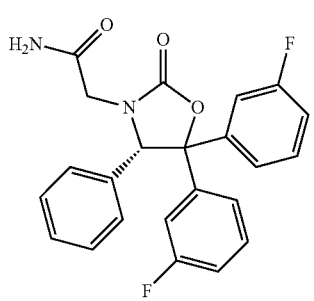 [SMILES: NC(=O)CN1C(=O)OC(c2cccc(F)c2)(c2cccc(F)c2)[C@@H]1c1ccccc1]

2-[(S)-5,5-Bis-(3-fluoro-phenyl)-2-oxo-4-phenyl-oxazolidin-3-yl]-acetamide

The title compound was prepared analogously to Example 2 from (S)-methyl 2-(tert-butoxycarbonylamino)-2-phenylacetate and 1-fluoro-3-iodobenzene. MS: (MH)⁺ 409.2

EXAMPLE 4

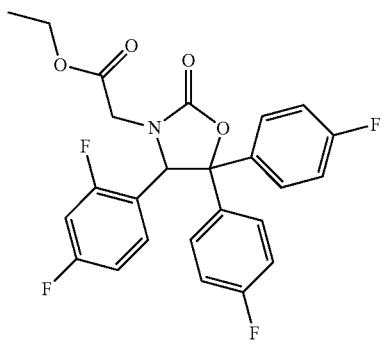 [SMILES: CCOC(=O)CN1C(=O)OC(c2ccc(F)cc2)(c2ccc(F)cc2)C1c1ccc(F)cc1F]

[4-(2,4-Difluoro-phenyl)-5,5-bis-(4-fluoro-phenyl)-2-oxo-oxazolidin-3-yl]-acetic acid ethyl ester A) tert-Butoxycarbonylamino-(2,4-difluoro-phenyl)-acetic acid methyl ester To methyl 2-amino-2-(2,4-difluorophenyl)acetate (2.7 g, 13.4 mmol) in methylene chloride (100 ml) was added di-tert-butyl dicarbonate (2.9 g, 13.4 mmol) and the reaction stirred for 16 h. It was then evaporated affording the title compound (4.2 g, 100%) in sufficient purity as to be used crude. MS: (MH)⁺ 302.2

B) [4-(2,4-Difluoro-phenyl)-5,5-bis-(4-fluoro-phenyl)-2-oxo-oxazolidin-3-yl]-acetic acid ethyl ester The title compound was prepared from tert-butoxycarbonylamino-(2,4-difluoro-phenyl)-acetic acid methyl ester and (4-fluorophenyl)magnesium bromide in analogy to example 2 (steps A, B, C) followed by example 1 step C. MS: (MH)⁺ 474.4

EXAMPLE 5

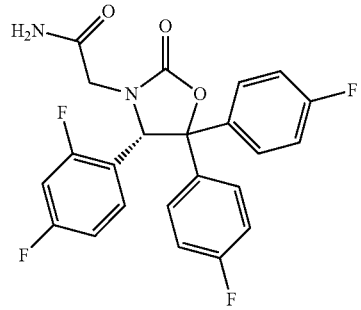

2-[(S)-4-(2,4-Difluoro-phenyl)-5,5-bis-(4-fluoro-phenyl)-2-oxo-oxazolidin-3-yl]-acetamide The title compound was prepared as the racemate from [4-(2,4-difluoro-phenyl)-5,5-bis-(4-fluoro-phenyl)-2-oxo-oxazolidin-3-yl]-acetic acid ethyl ester (Example 4) in analogy to example 1 (Steps D, E). Chiral separation was performed using Chiralpak® AD column (eluent Ethanol: n-Heptane 1:3) to afford the desired (−) isomer as a white solid. MS: (MH)⁺ 445.5.

EXAMPLE 6

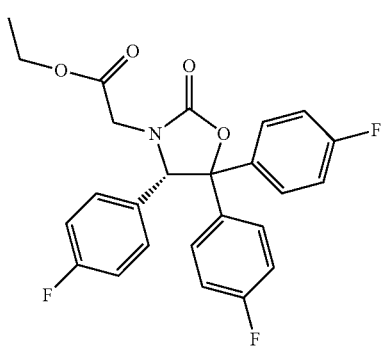 [SMILES: CCOC(=O)CN1C(=O)OC(c2ccc(F)cc2)(c2ccc(F)cc2)[C@@H]1c1ccc(F)cc1]

[(S)-4,5,5-Tris-(4-fluoro-phenyl)-2-oxo-oxazolidin-3-yl]acetic acid ethyl ester

The title compound was prepared from (S)-methyl 2-amino-2-(4-fluorophenyl)acetate and and (4-fluorophenyl)magnesium bromide in analogy to example 1 (Steps A, B, C) followed by example 1 step C, affording a white foam. MS: (MH)$^+$ 456.2.

EXAMPLE 7

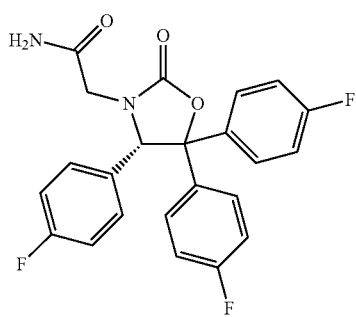 [SMILES: NC(=O)CN1C(=O)OC(c2ccc(F)cc2)(c2ccc(F)cc2)[C@@H]1c1ccc(F)cc1]

2-[(S)-4,5,5-Tris-(4-fluoro-phenyl)-2-oxo-oxazolidin-3-yl]-acetamide

The title compound was prepared from [(S)-4,5,5-tris-(4-fluoro-phenyl)-2-oxo-oxazolidin-3-yl]-acetic acid ethyl ester (Example 6) in analogy to example 1 (Steps D, E) affording a white foam. MS: (MH)$^+$ 427.3.

EXAMPLE 8

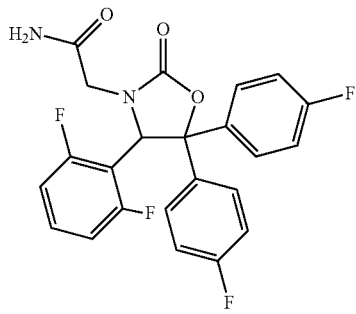 [SMILES: NC(=O)CN1C(=O)OC(c2ccc(F)cc2)(c2ccc(F)cc2)C1c1c(F)cccc1F]

2-[4-(2,6-Difluoro-phenyl)-5,5-bis-(4-fluoro-phenyl)-2-oxo-oxazolidin-3-yl]-acetamide A) Methyl 2-(tert-butoxycarbonylamino)-2-(2,6-difluorophenyl)acetate The title compound was prepared from methyl 2-amino-2-(2,6-difluorophenyl acetate) in analogy to example 4A affording a viscous oil. MS: (MH)$^+$ 302.2.

B) 2-[4-(2,6-Difluoro-phenyl)-5,5-bis-(4-fluoro-phenyl)-2-oxo-oxazolidin-3-yl]-acetamide The title compound was prepared from methyl 2-(tert-butoxycarbonylamino)-2-(2,6-difluorophenyl)acetate and (4-fluorophenyl)magnesium bromide in analogy to Example 2 to afford a white solid. MS: (MH)$^+$ 445.4.

EXAMPLE 9

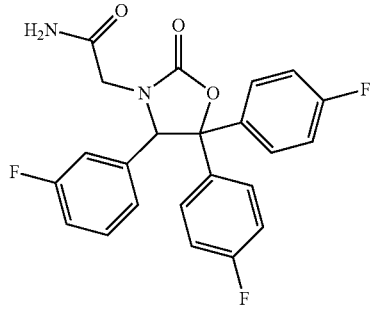 [SMILES: NC(=O)CN1C(=O)OC(c2ccc(F)cc2)(c2ccc(F)cc2)C1c1cccc(F)c1]

2-(4-(3-fluorophenyl)-5,5-bis(4-fluorophenyl)-2-oxooxazolidin-3-yl)acetamide

A) Methyl 2-(tert-butoxycarbonylamino)-2-(3-fluorophenyl)acetate

The title compound was prepared from methyl 2-amino-2-(3-fluorophenyl acetate) in analogy to example 4A affording a viscous oil. MS: (MH)$^+$ 284.2

B) 2-(4-(3-fluorophenyl)-5,5-bis(4-fluorophenyl)-2-oxooxazolidin-3-yl)acetamide

The title compound was prepared from methyl 2-(tert-butoxycarbonylamino)-2-(3-fluorophenyl)acetate and (4-fluorophenyl)magnesium bromide in analogy to Example 2 to afford a white solid. MS: (MH)$^+$ 427.3.

EXAMPLE 10

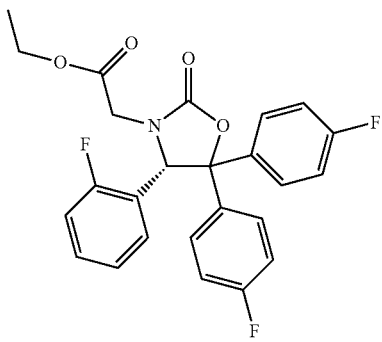 [SMILES: CCOC(=O)CN1C(=O)OC(c2ccc(F)cc2)(c2ccc(F)cc2)[C@@H]1c1ccccc1F]

[5,5-Bis-(4-fluoro-phenyl)-4-(2-fluoro-phenyl)-2-oxo-oxazolidin-3-yl]-acetic acid ethyl ester A) (S)-Methyl 2-(tert-butoxycarbonylamino)-2-(2-fluorophenyl)acetate The title compound was prepared from (S)-methyl 2-amino-2-(2-fluorophenyl)acetate in analogy to example 4A affording a colourless crystalline solid. MS: (MH)$^+$ 284.1.

B) (S)-4-(2-fluorophenyl)-5,5-bis(4-fluorophenyl) oxazolidin-2-one

The title compound was prepared from methyl 2-(tert-butoxycarbonylamino)-2-(2-fluorophenyl)acetate and (4-fluorophenyl)magnesium bromide in analogy to example 2 (Steps A, B, C) to afford a colourless solid. MS: (MH+MeCN)$^+$ 411.1.

C) [5,5-Bis-(4-fluoro-phenyl)-4-(2-fluoro-phenyl)-2-oxo-oxazolidin-3-yl]-acetic acid ethyl ester The title compound was prepared from (S)-4-(2-fluoro-phenyl)-5,5-bis(4-fluorophenyl)oxazolidin-2-one in analogy to example followed by example 1 step C affording a colourless gum. MS: (MH)$^+$ 456.2.

EXAMPLE 11

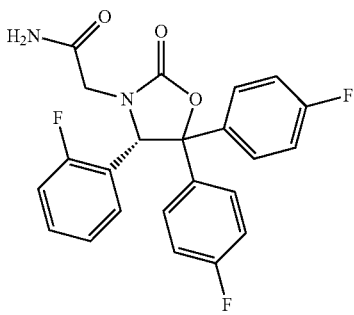 [SMILES: NC(=O)CN1C(=O)OC(c2ccc(F)cc2)(c2ccc(F)cc2)[C@@H]1c1ccccc1F]

2-[(S)-5,5-Bis-(4-fluoro-phenyl)-4-(2-fluoro-phenyl)-2-oxo-oxazolidin-3-yl]-acetamide To a solution of (S)-4-(2-fluorophenyl)-5,5-bis(4-fluorophenyl)oxazolidin-2-one (0.2 g, 0.5 mmol, Example 10 B) in THF (1 ml) under argon was added sodium hydride (0.03 g, 60% dispersion in mineral oil, 0.8 mmol). The reaction was stirred for 5 minutes after which time solid 2-bromoacetamide (0.1 g, 0.8 mmol) was added and the reaction stirred for a further 0.5 h. The reaction was poured onto 1 N hydrochloric acid, extracted with ethyl acetate, the organic phase was washed with water, brine, dried (Na$_2$SO$_4$) and concentrated. Purification by flash column chromatography (eluent EtOAc: n-Hept gradient 2:8-7:3) afforded the title compound as a colourless foam (0.2 g, 86%). MS: (MH)$^+$ 427.2.

EXAMPLE 12

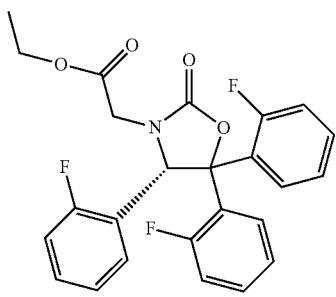 [SMILES: CCOC(=O)CN1C(=O)OC(c2ccccc2F)(c2ccccc2F)[C@@H]1c1ccccc1F]

[(S)-4,5,5-Tris-(2-fluoro-phenyl)-2-oxo-oxazolidin-3-yl]acetic acid ethyl ester

The title compound was prepared from (S)-methyl 2-(tert-butoxycarbonylamino)-2-(2-fluorophenyl)acetate (Example 11A) and and 1-fluoro-2-iodobenzene in analogy to example 2 (Steps A, B, C) followed by Step 1 C, affording a colourless gum. MS: (MH)$^+$ 456.1.

EXAMPLE 13

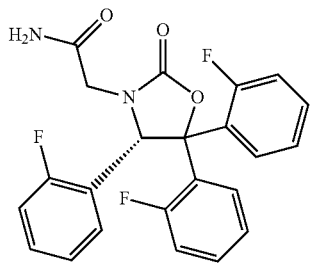 [SMILES: NC(=O)CN1C(=O)OC(c2ccccc2F)(c2ccccc2F)[C@@H]1c1ccccc1F]

2-[(S)-4,5,5-Tris-(2-fluoro-phenyl)-2-oxo-oxazolidin-3-yl]-acetamide

The title compound was prepared from [(S)-4,5,5-tris-(2-fluoro-phenyl)-2-oxo-oxazolidin-3-yl]-acetic acid ethyl ester (Example 12) in analogy to example 1 (Steps D, E) affording a white foam. MS: (MH)$^+$ 427.5.

EXAMPLE 14

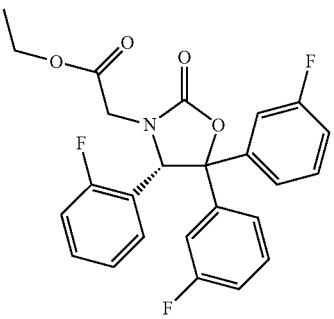 [SMILES: CCOC(=O)CN1C(=O)OC(c2cccc(F)c2)(c2cccc(F)c2)[C@@H]1c1ccccc1F]

[(S)-5,5-Bis-(3-fluoro-phenyl)-4-(2-fluoro-phenyl)-2-oxo-oxazolidin-3-yl]-acetic acid ethyl ester The title compound was prepared from (S)-methyl 2-(tert-butoxycarbonylamino)-2-(2-fluorophenyl)acetate (Example 11A) and and 1-fluoro-3-iodobenzene in analogy to example 2, affording a colourless gum. MS: (MH)$^+$ 456.5.

EXAMPLE 15

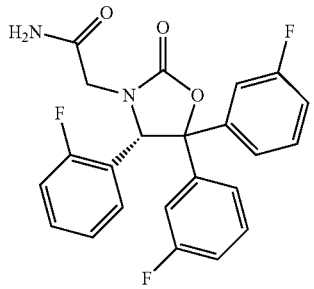 [SMILES: NC(=O)CN1C(=O)OC(c2cccc(F)c2)(c2cccc(F)c2)[C@@H]1c1ccccc1F]

2-[(S)-5,5-Bis-(3-fluoro-phenyl)-4-(2-fluoro-phenyl)-2-oxo-oxazolidin-3-yl]-acetamide The title compound was prepared from [(S)-5,5-bis-(3-fluoro-phenyl)-4-(2-fluoro-phenyl)-2-oxo-oxazolidin-3-yl]-acetic acid ethyl ester (Example 14) in analogy to example 1 (Steps D, E) affording a white foam. MS: (MH)$^+$ 427.4.

EXAMPLE 16

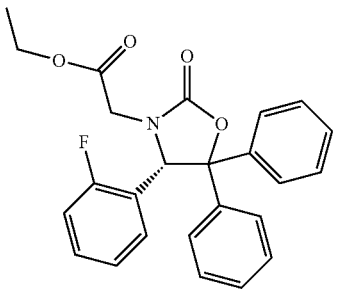 [SMILES: CCOC(=O)CN1C(=O)OC(c2ccccc2)(c2ccccc2)[C@@H]1c1ccccc1F]

[(S)-4-(2-Fluoro-phenyl)-2-oxo-5,5-diphenyl-oxazolidin-3-yl]-acetic acid ethyl ester The title compound was prepared from (S)-methyl 2-(tert-butoxycarbonylamino)-2-(2-fluorophenyl)acetate (Example 11A) and phenylmagnesium bromide in analogy to example 2(Steps A, B, C) followed by Step 1 C, affording a colourless gum. MS: (MH)+ 420.5.

EXAMPLE 17

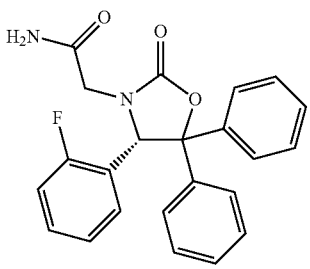 [SMILES: NC(=O)CN1C(=O)OC(c2ccccc2)(c2ccccc2)[C@@H]1c1ccccc1F]

2-[(S)-4-(2-Fluoro-phenyl)-2-oxo-5,5-diphenyl-oxazolidin-3-yl]-acetamide

The title compound was prepared from [(S)-4-(2-fluoro-phenyl)-2-oxo-5,5-diphenyl-oxazolidin-3-yl]-acetic acid ethyl ester (Example 16) in analogy to example 1 (Steps D, E) affording a white foam. MS: (MH)+ 391.5.

EXAMPLE 18

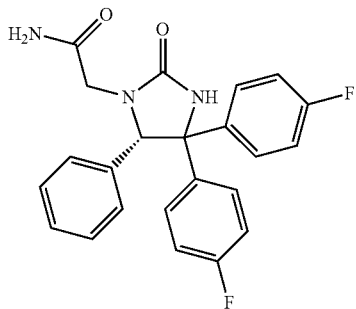 [SMILES: NC(=O)CN1C(=O)NC(c2ccc(F)cc2)(c2ccc(F)cc2)[C@@H]1c1ccccc1]

(S)-2-(4,4-bis(4-fluorophenyl)-2-oxo-5-phenylimidazolidin-1-yl)acetamide

A) (S)-1-(2,2-bis(4-fluorophenyl)-2-hydroxy-1-phenylethyl)-3-(2,4-dimethoxybenzyl)urea To a solution of (S)-2-amino-1,1-bis(4-fluorophenyl)-2-phenylethanol (Example 1A) (0.75 g, 2.3 mmol) in methylene chloride (10 ml) was added 1-(isocyanatomethyl)-2,4-dimethoxybenzene (0.53 g, 2.8 mmol) and the reaction stirred for 1 h. The mixture was then absorbed onto silica gel and purified by flash column chromatography (eluent gradient EtOAc: n-Hept 1:9-1:1) to afford the title product as a colourless crystalline solid (0.89 g, 75%). MS: (MH)+ 518.5.

B) (S)-4,4-bis(4-fluorophenyl)-5-phenylimidazolidin-2-one

To a suspension of (S)-1-(2,2-bis(4-fluorophenyl)-2-hydroxy-1-phenylethyl)-3-(2,4-dimethoxybenzyl)urea (0.89 g, 1.7 mmol) in methylene chloride (5 ml) in a sealed tube was added boron trifluoride etherate (0.4 ml, 3.4 mmol) an the mixture heated to 50° C. for 3 h. The reaction was then diluted with methylene chloride and washed with saturated sodium hydrogen carbonate solution, dried (Na2SO4) and concentrated. Purification by flash column chromatography (eluent EtOAc: n-Hept gradient 1:1-1:0) afforded the title compound as a colourless gum (0.48 g, 80%). MS: (MH)+ 351.2.

C) (S)-2-(4,4-bis(4-fluorophenyl)-2-oxo-5-phenylimidazolidin-1-yl)-N,N-bis(2,4-dimethoxybenzyl)acetamide To an ice-cold solution of 2-chloro-N,N-bis(2,4-dimethoxybenzyl)acetamide (0.17 g. 0.4 mmol, prepared by the reaction of 2-chloroacetic anhydride and bis(2,4-dimethoxybenzyl)amine MS: (MH, Cl)+ 394.1) and (S)-4,4-bis(4-fluorophenyl)-5-phenylimidazolidin-2-one (0.1 g, 0.3 mmol) in anhydrous THF (3 ml) was added sodium hydride (0.03 g, 60% dispersion in mineral oil, 0.6 mmol) and the reaction stirred for 1 h at 0° C. and 1 h at ambient temperature. The reaction was then diluted with ethyl acetate, washed with 1N HCl, brine, dried (Na2SO4) and concentrated. Purification by flash column chromatography (eluent EtOAc: MeOH gradient 1:0-1:9) afforded the title compound as a colourless gum (0.2 g, 50%). MS: (MH)+ 708.6.

D) (S)-2-(4,4-bis(4-fluorophenyl)-2-oxo-5-phenylimidazolidin-1-yl)acetamide

To a solution of (S)-2-(4,4-bis(4-fluorophenyl)-2-oxo-5-phenylimidazolidin-1-yl)-N,N-bis(2,4-dimethoxybenzyl)acetamide (0.1 g, 0.1 mmol) in methylene chloride (2 ml) was added borontrifluoride etherate (0.04 ml, 0.3 mmol) and the mixture stirred for 6 h. More borontrifluoride etherate (0.04 ml, 0.3 mmol) was added and the mixture stirred overnight after which time the reaction was diluted with methylene chloride, washed with saturated sodium hydrogen carbonate solution, dried (Na2SO4) and concentrated. The residue was purified by preparative HPLC to afford the title compound as a colourless solid (0.02 g, 33%). MS: (MH)+ 408.3.

EXAMPLE 19

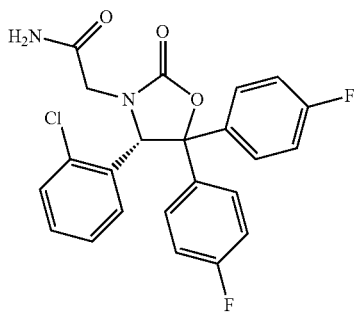

2-[(S)-4-(2-Chloro-phenyl)-5,5-bis-(4-fluoro-phenyl)-2-oxo-oxazolidin-3-yl]-acetamide A) (S)-Methyl 2-(tert-butoxycarbonylamino)-2-(2-chlorophenyl)acetate The title compound was prepared from (S)-methyl 2-amino-2-(2-chlorophenyl)acetate in analogy to example 4A affording a light brown gum. MS: (MH-Boc, Cl)$^+$ 200.2

B) [5,5-Bis-(4-fluoro-phenyl)-4-(2-chloro-phenyl)-2-oxo-oxazolidin-3-yl]-acetic acid ethyl ester The title compound was prepared from methyl 2-(tert-butoxycarbonylamino)-2-(2-fluorophenyl)acetate and (4-fluorophenyl)magnesium bromide in analogy to example 2 affording a crystalline solid. MS: (MH)$^+$ 456.2.

EXAMPLE 20

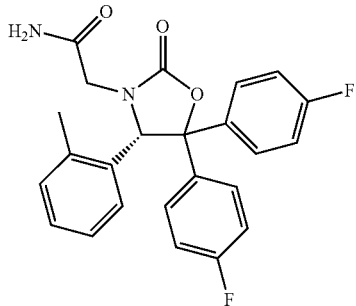

2-[(S)-5,5-Bis-(4-fluoro-phenyl)-2-oxo-4-o-tolyl-oxazolidin-3-yl]-acetamide

A) (Methyl 2-(tert-butoxycarbonylamino)-2-o-tolylacetate

The title compound was prepared from methyl 2-amino-2-o-tolylacetate hydrochloride in analogy to example 4A affording a light yellow gum. MS: (MH-Boc)$^+$ 180.2

B) [5,5-Bis-(4-fluoro-phenyl)-4-(2-chloro-phenyl)-2-oxo-oxazolidin-3-yl]-acetic acid ethyl ester The title compound was prepared from methyl 2-(tert-butoxycarbonylamino)-2-o-tolylacetate and (4-fluorophenyl)magnesium bromide in analogy to example 2, affording a crystalline solid. Chiral separation was performed using Chiralpak® AD column (eluent iso-Propanol: n-Heptane 1:9) to afford the desired (−) isomer as a white solid. MS: (MH)$^+$ 423.5.

EXAMPLE 21

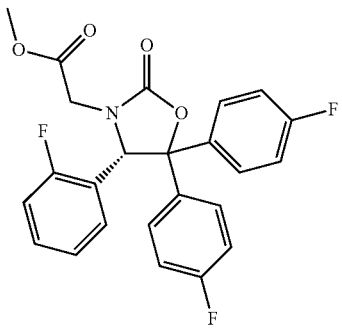 [SMILES: COC(=O)CN1C(=O)OC(c2ccc(F)cc2)(c2ccc(F)cc2)[C@@H]1c1ccccc1F]

(S)-methyl 2-(4-(2-fluorophenyl)-5,5-bis(4-fluorophenyl)-2-oxooxazolidin-3-yl)acetate The title compound was prepared from (S)-4-(2-fluorophenyl)-5,5-bis(4-fluorophenyl)oxazolidin-2-one (Example 10 B) in analogy to step 10 C and bromoacetic acid methyl ester to afford a colourless gum. MS: (MH)$^+$ 442.3.

EXAMPLE 22

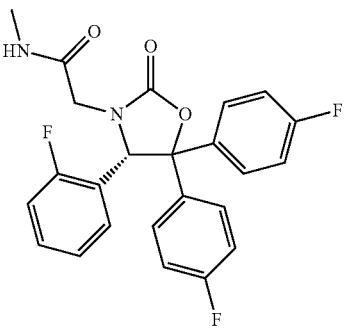 [SMILES: CNC(=O)CN1C(=O)OC(c2ccc(F)cc2)(c2ccc(F)cc2)[C@@H]1c1ccccc1F]

(S)-2-(4-(2-fluorophenyl)-5,5-bis(4-fluorophenyl)-2-oxooxazolidin-3-yl)-N-methylacetamide A) [5,5-Bis-(4-fluoro-phenyl)-4-(2-fluoro-phenyl)-2-oxo-oxazolidin-3-yl]-acetic acid The title compounds was prepared from [5,5-bis-(4-fluoro-phenyl)-4-(2-fluoro-phenyl)-2-oxo-oxazolidin-3-yl]-acetic acid ethyl ester (Example 10) in analogy to step 1D affording a white foam. MS: (MH)$^+$ 428.4.

B) (S)-2-(4-(2-fluorophenyl)-5,5-bis(4-fluorophenyl)-2-oxooxazolidin-3-yl)-N-methylacetamide To a solution [5,5-bis-(4-fluoro-phenyl)-4-(2-fluoro-phenyl)-2-oxo-oxazolidin-3-yl]-acetic acid (50 mg, 0.10 mmol) and 2-(1H-benzotriazole1-yl)-1,1,3,3-tetramethylurononium tetrafluoroborate (41 mg, 0.13 mmol) in dimethylformamide (0.5 ml) was added di-isopropylethylamine (0.1 ml, 0.59 mmol) followed by methylamine hydrochloride (9 mg, 0.13 mmol). The mixture was stirred at room temperature for 1 h, after which time the reaction was poured onto 1 N hydrochloric acid and extracted with ethyl acetate. The organic phase was washed with brine, dried (Na$_2$SO$_4$) and concentrated. Purification by flash column chromatography (eluent EtOAc: n-Heptane gradient 0:1-1:1) afforded the title compound as a colourless gum (23 mg, 45%). MS: (MH)$^+$ 441.5.

EXAMPLE 23

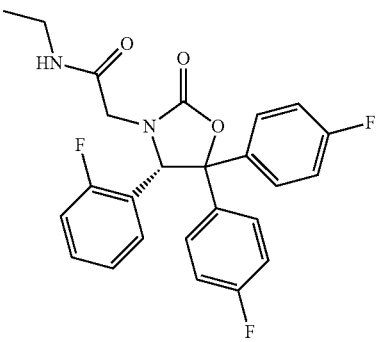 [SMILES: CCNC(=O)CN1C(=O)OC(c2ccc(F)cc2)(c2ccc(F)cc2)[C@@H]1c1ccccc1F]

(S)—N-ethyl-2-(4-(2-fluorophenyl)-5,5-bis(4-fluorophenyl)-2-oxooxazolidin-3-yl)acetamide The title compound was prepared in analogy to example 22 from [5,5-bis-(4-fluoro-phenyl)-4-(2-fluoro-phenyl)-2-oxo-oxazolidin-3-yl]-acetic acid (Example 22A) and ethylamine hydrochloride to afford a colourless gum. MS: (MH)$^+$ 455.5.

EXAMPLE 24

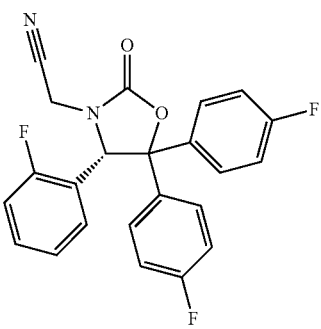 [SMILES: N#CCN1C(=O)OC(c2ccc(F)cc2)(c2ccc(F)cc2)[C@@H]1c1ccccc1F]

[(S)-5,5-Bis-(4-fluoro-phenyl)-4-(2-fluoro-phenyl)-2-oxo-oxazolidin-3-yl]-acetonitrile To a mixture of (S)-4-(2-fluorophenyl)-5,5-bis(4-fluorophenyl)oxazolidin-2-one (0.035 g, 0.09 mmol) (Example 10B) and 3-(chloromethyl)-1,2,4-oxadiazole (0.015 g, 0.12 mmol) in THF under argon was added sodium hydride (0.008 g, 60% dispersion in mineral oil, 0.19 mmol) and the reaction stirred for 24 h. After which time the mixture was neutralized with Amberlite® IR120 resin, filtered and concentrated. Purification by recrystallization from 20% EtOAc/n-Heptane afforded the titled product as white crystals. MS: (MH)$^+$ 408.1.

EXAMPLE 25

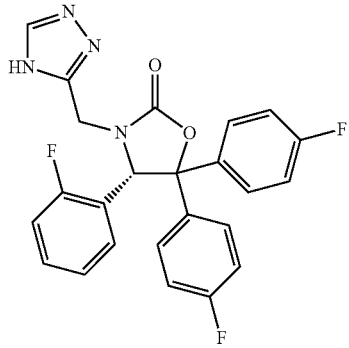 [SMILES: O=C1OC(c2ccc(F)cc2)(c2ccc(F)cc2)[C@H](c2ccccc2F)N1Cc1nnc[nH]1]

(S)-3-((4H-1,2,4-triazol-3-yl)methyl)-4-(2-fluorophenyl)-5,5-bis(4-fluorophenyl)oxazolidin-2-one A) (S)-2-(4-(2-fluorophenyl)-5,5-bis(4-fluorophenyl)-2-oxooxazolidin-3-yl)acetohydrazide To a solution of [5,5-Bis-(4-fluoro-phenyl)-4-(2-fluoro-phenyl)-2-oxo-oxazolidin-3-yl]-acetic acid ethyl ester (0.17 g, 0.36 mmol, Example 10) in ethanol (3 ml) was added hydrazine monohydrate (0.18 ml, 3.62 mmol) and the mixture heated to 80° C. for 2 h. The mixture was then evaporated to dryness affording the titled compound as a colourless foam (0.16 g, 100%). MS: (MH)$^+$ 442.3.

B) (S)-3-((4H-1,2,4-triazol-3-yl)methyl)-4-(2-fluorophenyl)-5,5-bis(4-fluorophenyl)oxazolidin-2-one To a solution of (S)-2-(4-(2-fluorophenyl)-5,5-bis(4-fluorophenyl)-2-oxooxazolidin-3-yl)acetohydrazide (0.05 g, 0.1 mmol) in NMP (0.6 ml) was added ethyl formimidate hydrochloride (0.06 g, 0.6 mmol) and the mixture heated to 200° C. in a microwave for 15 minutes. The reaction was then diluted with ethyl acetate, washed repeatedly with water, brine, dried (Na$_2$SO$_4$) and concentrated. Purification by flash column chromatography (eluent EtOAc: n-Heptane gradient 4:6-7:3) afforded the title compound as a crystalline solid (8 mg, 15%). MS: (MH)$^+$ 451.3.

EXAMPLE 26

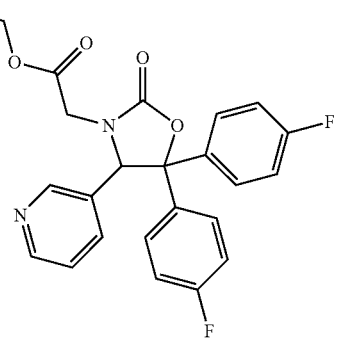

Ethyl 2-(5,5-bis(4-fluorophenyl)-2-oxo-4-(pyridin-3-yl)oxazolidin-3-yl)acetate

A) Ethyl 2-(tert-butoxycarbonylamino)-2-(pyridin-3-yl)acetate

The title compound was prepared from ethyl 2-amino-2-(pyridin-3-yl)acetate in analogy to example 4A affording a colourless crystalline solid. MS: (MH)$^+$ 284.1.

B) Ethyl 2-(5,5-bis(4-fluorophenyl)-2-oxo-4-(pyridin-3-yl)oxazolidin-3-yl)acetate The title compound was prepared from ethyl 2-(tert-butoxycarbonylamino)-2-(pyridin-3-yl)acetate and (4-fluorophenyl)magnesium bromide in analogy to example 1 (Steps A, B, C) followed by example 1 step C, affording an orange foam. MS: (MH)+ 439.4.

EXAMPLE 27

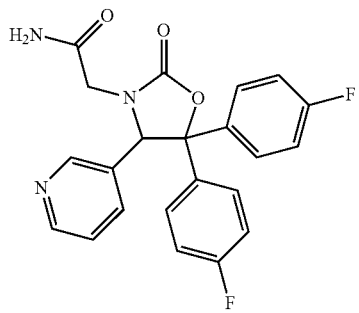 [SMILES: NC(=O)CN1C(=O)OC(c2ccc(F)cc2)(c2ccc(F)cc2)C1c1cccnc1]

2-(5,5-bis(4-fluorophenyl)-2-oxo-4-(pyridin-3-yl)oxazolidin-3-yl)acetamide

The title compound was prepared from ethyl 2-(5,5-bis (4-fluorophenyl)-2-oxo-4-(pyridin-3-yl)oxazolidin-3-yl)acetate (Example 26) in analogy to example 1 (Steps D, E) affording a white foam. MS: (MH)+ 410.4.

EXAMPLE 28

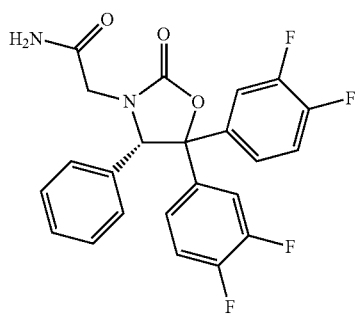 [SMILES: NC(=O)CN1C(=O)OC(c2ccc(F)c(F)c2)(c2ccc(F)c(F)c2)[C@@H]1c1ccccc1]

(S)-2-(5,5-bis(3,4-difluorophenyl)-2-oxo-4-phenyloxazolidin-3-yl)acetamide

A) (S)-ethyl 2,2-bis(3,4-difluorophenyl)-2-hydroxy-1-phenylethylcarbamate

Prepared from (S)-methyl 2-(ethoxycarbonylamino)-2-phenylacetate and the Grignard prepared from 1,2-difluoro-4-iodobenzene in analogy to Example 2A to afford the title compound as a white foam. MS: (M-OH)+ 416.

B) (S)-5,5-bis(3,4-difluorophenyl)-4-phenyloxazolidin-2-one

To a solution of (S)-ethyl 2,2-bis(3,4-difluorophenyl)-2-hydroxy-1-phenylethylcarbamate (1.5 g, 3.5 mmol) in EtOH was added potassium tert-butylate (0.4 g, 3.5 mmol) and the reaction mixture was stirred at 80° C. for 30 min. The reaction was then acidified with Amberlite® IR120 resin, filtered and concentrated to afford the title compound as white solid (1.2 g, 89%). MS: (M–H)− 386.5.

C) (S)-2-(5,5-bis(3,4-difluorophenyl)-2-oxo-4-phenyloxazolidin-3-yl)acetamide

The title compound was prepared from (S)-5,5-bis(3,4-difluorophenyl)-4-phenyloxazolidin-2-one in analogy to Example 1 (Steps C, D, E) to afford a white foam. MS: (MH)+ 445.3.

EXAMPLE 29

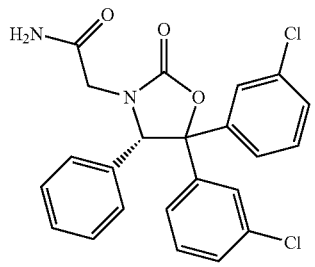 [SMILES: NC(=O)CN1C(=O)OC(c2cccc(Cl)c2)(c2cccc(Cl)c2)[C@@H]1c1ccccc1]

2-[(S)-5,5-Bis-(3-chloro-phenyl)-2-oxo-4-phenyl-oxazolidin-3-yl]-acetamide

The title compound was prepared from (S)-methyl 2-(ethoxycarbonylamino)-2-phenylacetate and (3-chlorophenyl)magnesium bromide in analogy to Example 28 to afford a white solid. MS: (MH, 2Cl)+ 441.3.

EXAMPLE 30

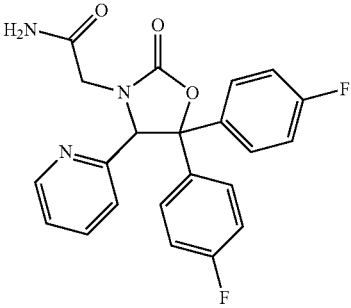 [SMILES: NC(=O)CN1C(=O)OC(c2ccc(F)cc2)(c2ccc(F)cc2)C1c1ccccn1]

2-(5,5-bis(4-fluorophenyl)-2-oxo-4-(pyridin-2-yl)oxazolidin-3-yl)acetamide

The title compound was prepared from ethyl 2-amino-2-(pyridin-2-yl)acetate in analogy to example 27 to afford a colourless gum. MS: (MH)+ 410.5.

EXAMPLE 31

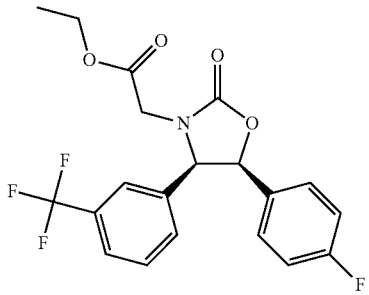 [SMILES: CCOC(=O)CN1C(=O)O[C@@H](c2ccc(F)cc2)[C@H]1c1cccc(C(F)(F)F)c1]

[(4RS,5SR)-5-(4-Fluoro-phenyl)-2-oxo-4-(3-trifluoromethyl-phenyl)-oxazolidin-3-yl]-acetic acid ethyl ester

A) (4-fluorophenyl)(2-(3-(trifluoromethyl)phenyl)-1,3-dithian-2-yl)methanol

To a solution of 2-(3-(trifluoromethyl)phenyl)-1,3-dithiane (2.00 g, 7.57 mmol, *J. Organometallic Chem.* 2000, 220) in THF (40 mL) was added n-BuLi (5.2 mL, 8.32 mmol, 1.6 M in hexane) at −78° C. It was stirred at −78° C. for 2 h, then a solution of 4-fluorobenzaldehyde (0.85 mL, 7.8 mmol) in THF (6 mL) was added. The mixture was stirred at −78° C. for 1 h and then allowed to warm up to ambient temperature. It was then poured onto saturated ammonium chloride solution. The mixture was was extracted with EtOAc. The combined organic layers were washed with brine, dried (Na$_2$SO$_4$) and concentrated. Purification by flash column chromatography (eluent EtOAc: n-Heptane gradient 0:1-3:7) afforded the title compound as a colourless gum (2.70 g, 92%). MS: (M+NH$_4$)$^+$ 406.3.

B) 2-(4-fluorophenyl)-2-hydroxy-1-(3-(trifluoromethyl)phenyl)ethanone

To a solution of (4-fluorophenyl)(2-(3-(trifluoromethyl)phenyl)-1,3-dithian-2-yl)methanol (2.67 g, 6.9 mmol) in acetonitrile (12 mL) and water (2 mL) was dropwise added a solution of [bis(trifluoroacetoxy)iodo]benzene (4.43 g, 10.3 mmol) in acetonitrile (8 mL), The reaction was stirred at ambient temperature for 1 h, then cautiously poured onto saturated sodium hydrogen carbonate solution. The mixture was extracted with EtOAc. The combined organic layers were washed with brine, dried (Na$_2$SO$_4$) and concentrated. Purification by flash column chromatography (eluent EtOAc: n-Heptane gradient 0:1-4:6) afforded the title compound as a colourless oil (0.5 g, 25%). MS: (M−H)$^−$ 297.2.

C) (2-(4-fluorophenyl)-2-hydroxy-1-(3-(trifluoromethyl)phenyl)ethanone O-benzyl oxime To a solution of 2-(4-fluorophenyl)-2-hydroxy-1-(3-(trifluoromethyl)phenyl)ethanone (487 mg, 1.6 mmol) and O-benzylhydroxylamine hydrochloride (287 mg, 1.8 mmol) in THF (7 mL) and water (3 mL) was added sodium acetate (147 mg, 1.8 mmol). The reaction was heated to reflux for 12 h, then cooled and partitioned between EtOAc and water. The mixture was extracted repeatedly with EtOAc and the combined organic layers were washed with brine, dried (Na$_2$SO$_4$) and concentrated. Purification by flash column chromatography (eluent EtOAc: n-Heptane gradient 0:1-3:7) afforded the title compound as a colourless oil (603 mg, 92%). MS: (M+H)$^+$ 404.3.

D) (1SR,2RR)-2-amino-1-(4-fluorophenyl)-2-(3-(trifluoromethyl)phenyl)ethanol To a solution of (2-(4-fluorophenyl)-2-hydroxy-1-(3-(trifluoromethyl)phenyl)ethanone O-benzyl oxime (200 mg, 0.5 mmol) in methanol (5 mL) was added 10% Pd/C. The mixture was stirred under 1 atmosphere (balloon) of hydrogen for 16 h after which time it was filtered over Hyflo and concentrated to afford the title compound as a colourless oil (111 mg, 75%). MS: (M+H)$^+$ 300.2

E) [(4RS,5SR)-5-(4-Fluoro-phenyl)-2-oxo-4-(3-trifluoromethyl-phenyl)-oxazolidin-3-yl]-acetic acid ethyl ester The title compound was prepared from (1SR,2RR)-2-amino-1-(4-fluorophenyl)-2-(3-(trifluoromethyl)phenyl)ethanol in analogy to Example 1 (steps B, C). MS: (M+H)$^+$ 412.3.

EXAMPLE 32

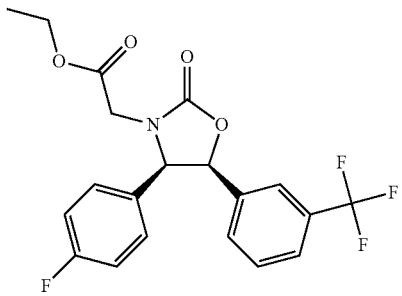 [SMILES: CCOC(=O)CN1C(=O)O[C@@H](c2cccc(C(F)(F)F)c2)[C@H]1c1ccc(F)cc1]

[(4RS,5SR)-4-(4-Fluoro-phenyl)-2-oxo-5-(3-trifluoromethyl-phenyl)-oxazolidin-3-yl]-acetic acid ethyl ester

A) tert-butyl 1-(4-fluorophenyl)-2-(methoxy(methyl)amino)-2-oxoethylcarbamate To a mixture of 2-(tert-butoxycarbonylamino)-2-(4-fluorophenyl)acetic acid (14.5 g, 54 mmol), N,O-dimethylhydroxylamine hydrochloride (8.4 g, 86 mmol), N-methylmorpholine (9.5 mL, 86 mmol) and dimethylaminopyridine (0.7 g, 5 mmol) in dichloromethane (150 mL) and dimethylformamide (32 mL) at 0° C. was added 1-ethyl-3-(3-dimethylaminopropyl)carbodiimide (12.4 g, 5 mmol). The reaction was allowed to warm up to room temperature and stirred for 2 h, then poured onto cold 1 N hydrochloric acid and extracted with EtOAc. The organic layers were washed with water, saturated sodium hydrogen carbonate solution, brine, dried (Na$_2$SO$_4$) and concentrated to afford the title compound as a white solid (14.5 g, 99%). MS: (M+H)$^+$ 313.4.

B) tert-butyl 1-(4-fluorophenyl)-2-oxo-2-(3-(trifluoromethyl)phenyl)ethylcarbamate 3-Iodobenzotrifluoride (2.3 mL, 16 mmol) was added dropwise to iso-propylmagnesium chloride-lithium chloride (12.3 mL, 16 mmol, 1.3 M in THF) maintaining the temperature below 40° C. by using a water bath. After 30 minutes was added to a solution of tert-butyl 1-(4-fluorophenyl)-2-(methoxy(methyl)amino)-2-oxoethylcarbamate (2.00 g, 6.4 mmol) in THF (26 mL) at 0° C. The reaction was stirred at 0° C. for 15 min and at room temperature for 1 h, then poured onto saturated ammonium chloride solution and extracted with EtOAc. The organic layers were washed with brine, dried (Na$_2$SO$_4$) and concentrated. Purification by flash column chromatography (eluent EtOAc: n-Heptane gradient 0:1-1:1) afforded the title compound as a white solid (2.42 g, 95%). MS: (M−H)$^−$ 396.4.

C) tert-butyl (1RS,2SR)-1-(4-fluorophenyl)-2-hydroxy-2-(3-(trifluoromethyl)phenyl)ethylcarbamate To a solution of tert-butyl 1-(4-fluorophenyl)-2-oxo-2-(3-(trifluoromethyl)phenyl)ethylcarbamate (2.4 g, 6.0 mmol) in methanol (40 mL) was added sodium borohydride (248 mg, 6.6 mmol), bubbling. Mixture was stirred at room temperature for 30 minutes. The mixture was poured onto water and stirred for 10 minutes, then filtered, washed with water and dried give product as white solid (2.23 g 95%). MS: (M−H)$^−$ 398.5

D) (1 SR,2RS)-2-amino-2-(4-fluorophenyl)-1-(3-(trifluoromethyl)phenyl)ethanol

To a suspension of tert-butyl (1RS,2SR)-1-(4-fluorophenyl)-2-hydroxy-2-(3-(trifluoromethyl)phenyl)ethylcarbamate (2.2 g, 5.6 mmol) in dichloromethane (35 mL) was added trifluoroacetic acid (4.8 mL, 62.5 mmol). The reaction was stirred at room temperature for 90 minutes, and then cautiously poured onto saturated sodium hydrogen carbonate solution and extracted with dichloromethane. The organic layers were washed with brine, dried dried (Na$_2$SO$_4$) and concentrated to give the titled product as colorless gum (1.8 g, 100%). MS: (M+H)$^+$ 300.4

E) (4RS,5SR)-4-(4-fluorophenyl)-5-(3-(trifluoromethyl)phenyl)oxazolidin-2-one

A solution (1SR,2RS)-2-amino-2-(4-fluorophenyl)-1-(3-(trifluoromethyl)phenyl)ethanol (1.7 g, 5.7 mmol) and triethylamine (2.4 mL, 16.9 mmol) in dichloromethane (45 mL) was cooled to 0° C. Then diphosgene (375 µl, 3.1 mmol) in dichloromethane (5 mL) was added. The reaction was stirred at 0° C. for 30 minutes, then partitioned between 1 M hydrochloric acid and dichloromethane. The organic layers were washed with brine, dried dried (Na$_2$SO$_4$) and concentrated. Purification by flash column chromatography (eluent EtOAc: n-Heptane gradient 0:1-1:0) afforded the title compound as a white solid (1.4 g, 77%). MS: (M+H)$^+$ 326.4.

F) [(4RS,5SR)-4-(4-Fluoro-phenyl)-2-oxo-5-(3-trifluoromethyl-phenyl)-oxazolidin-3-yl]-acetic acid ethyl ester The title compound was prepared in analogy to Example 1 step C from (4RS,5SR)-4-(4-fluorophenyl)-5-(3-(trifluoromethyl)phenyl)oxazolidin-2-one. MS: (M+H)$^+$ 412.2.

EXAMPLE 33

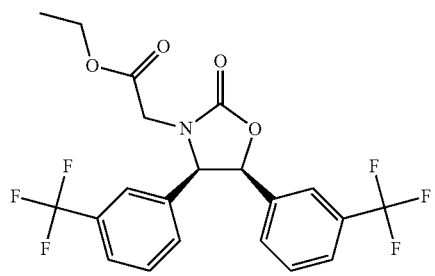 [SMILES: CCOC(=O)CN1C(=O)O[C@@H](c2cccc(C(F)(F)F)c2)[C@H]1c1cccc(C(F)(F)F)c1]

(4RS,5SR)-2-Oxo-4,5-bis-(3-trifluoromethyl-phenyl)-oxazolidin-3-yl]-acetic acid ethyl ester The title compound was prepared in analogy to example 31 starting from 2-(3-(trifluoromethyl)phenyl)-1,3-dithiane and 3-(trifluoromethyl)benzaldehyde. MS: (M+H)$^+$ 462.0.

EXAMPLE 34

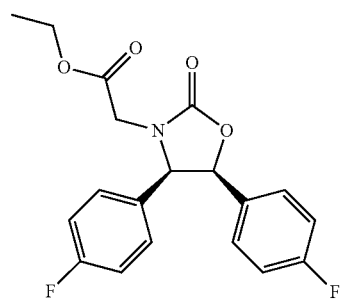 [SMILES: CCOC(=O)CN1C(=O)O[C@@H](c2ccc(F)cc2)[C@H]1c1ccc(F)cc1]

(4RS,5SR)-2-Oxo-4,5-bis-(4-fluorophenyl)-oxazolidin-3-yl]-acetic acid ethyl ester The title compound was prepared in analogy to example 31 starting from 2-(4-fluorophenyl)-1,3-dithiane and 4-fluorobenzaldehyde. MS: (M+H)$^+$ 362.2.

EXAMPLE 35

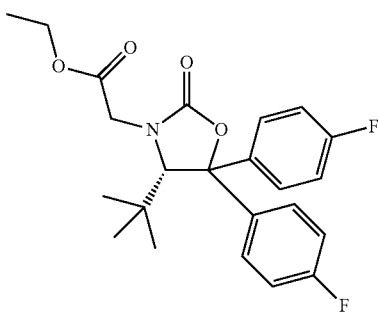 [SMILES: CCOC(=O)CN1C(=O)OC(c2ccc(F)cc2)(c2ccc(F)cc2)[C@@H]1C(C)(C)C]

[(S)-4-tert-Butyl-5,5-bis-(4-fluoro-phenyl)-2-oxo-oxazolidin-3-yl]-acetic acid ethyl ester The title compound was prepared in analogy to example 4 (S)-methyl 2-amino-3,3-dimethylbutanoate hydrochloride. MS: (M+H)$^+$ 417.4.

EXAMPLE 36

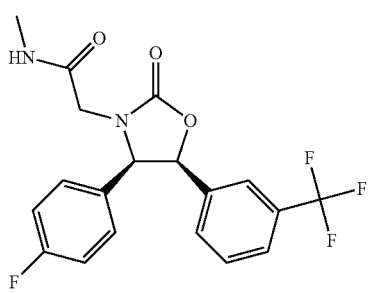 [SMILES: CNC(=O)CN1C(=O)O[C@@H](c2cccc(C(F)(F)F)c2)[C@H]1c1ccc(F)cc1]

2-(4RS,5SR)-4-(4-fluorophenyl)-2-oxo-5-(3-(trifluoromethyl)phenyl)oxazolidin-3-yl)-N-methylacetamide The title compound was prepared from [(4RS,5SR)-4-(4-Fluoro-phenyl)-2-oxo-5-(3-trifluoromethyl-phenyl)-oxazolidin-3-yl]-acetic acid ethyl ester (Example 32E) in analogy to example 22. MS: (M+H)$^+$ 397.4.

EXAMPLE 37

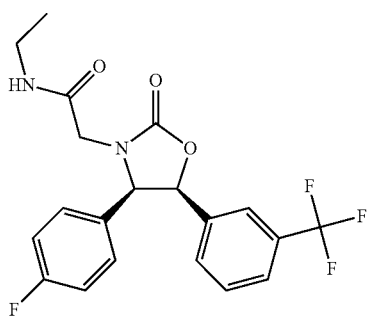 [SMILES: CCNC(=O)CN1C(=O)O[C@@H](c2cccc(C(F)(F)F)c2)[C@H]1c1ccc(F)cc1]

N-ethyl-2-(4RS,5SR)-4-(4-fluorophenyl)-2-oxo-5-(3-(trifluoromethyl)phenyl)oxazolidin-3-yl)acetamide The title compound was prepared from [(4RS,5SR)-4-(4-Fluoro-phenyl)-2-oxo-5-(3-trifluoromethyl-phenyl)-oxazolidin-3-yl]-acetic acid ethyl ester (Example 32E) in analogy to example 23. MS: (M+H)$^+$ 411.4.

EXAMPLE 38

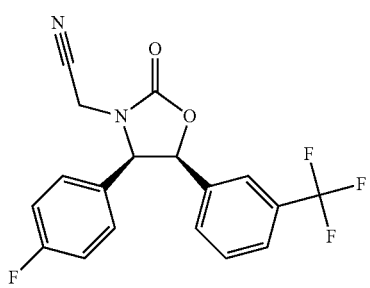 [SMILES: N#CCN1C(=O)O[C@@H](c2cccc(C(F)(F)F)c2)[C@H]1c1ccc(F)cc1]

2-(4RS,5SR)-4-(4-fluorophenyl)-2-oxo-5-(3-(trifluoromethyl)phenyl)oxazolidin-3-yl)acetonitrile The title compound was prepared from [(4RS,5SR)-4-(4-Fluoro-phenyl)-2-oxo-5-(3-trifluoromethyl-phenyl)-oxazolidin-3-yl]-acetic acid ethyl ester (Example 32E) in analogy to example 24. MS: (M+H)$^+$ 365.4.

EXAMPLE 39

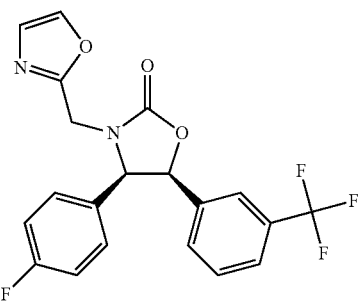 [SMILES: O=C1O[C@@H](c2cccc(C(F)(F)F)c2)[C@@H](c2ccc(F)cc2)N1Cc1ncco1]

(4RS,5SR)-4-(4-fluorophenyl)-3-(oxazol-2-ylmethyl)-5-(3-(trifluoromethyl)phenyl)oxazolidin-2-one The title compound was prepared from [(4RS,5SR)-4-(4-Fluoro-phenyl)-2-oxo-5-(3-trifluoromethyl-phenyl)-oxazolidin-3-yl]-acetic acid ethyl ester (Example 32E) and 2-(chloromethyl)oxazole in analogy to example 24. MS: (M+H)$^+$ 407.5.

EXAMPLE 40

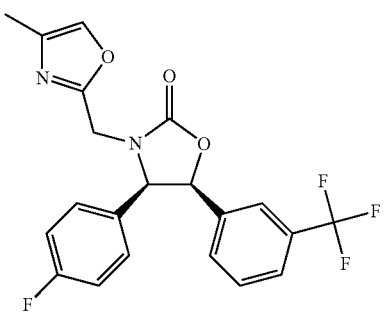 [SMILES: Cc1coc(CN2C(=O)O[C@@H](c3cccc(C(F)(F)F)c3)[C@H]2c2ccc(F)cc2)n1]

((4RS,5SR)-4-(4-fluorophenyl)-3-((4-methyloxazol-2-yl)methyl)-5-(3-(trifluoromethyl)phenyl)oxazolidin-2-one The title compound was prepared from [(4RS,5SR)-4-(4-Fluoro-phenyl)-2-oxo-5-(3-trifluoromethyl-phenyl)-oxazolidin-3-yl]-acetic acid ethyl ester (Example 32E) and 2-(chloromethyl)-5-methyloxazole in analogy to example 24. MS: (M+H)$^+$ 421.4.

KCa3.1 Channel Blockade Assays;
Thallium Influx Assay

The thallium influx assay was performed with CHOK1 cells over-expressing KCa3.1 obtained from Evotec and maintained in MEM Alpha medium supplemented with 10% fetal bovine serum, 100 U/ml penicillin/100 mg/ml streptomycin and 250 µg/ml G418.

CHOK1 wild type cells were passaged using F12/Ham's medium supplemented with 10% fetal bovine serum, 2 mM glutamine, 100 U/ml penicillin/100 mg/ml streptomycin. All cells were cultured in T175 flasks.

Before the day of the assay, cells were harvested from culture flasks using standard trypsin digestion. Cells were counted and densities adjusted and dispensed into 384-well poly-D-lysine coated plates at 7500 cells/SOW/well, assay plates were incubated overnight in $CO_2$ incubator at 37° C.

The following day, growth media was removed followed by the addition of 25 ul/well of FluxOR™ (Invitrogen) loading dye in a gluconate based assay buffer (135 mM NaGluconate, 2.5 mM Kgluconate, 2 mM CaNO3, 1 mM MgNO3, 10 mM HEPES (acid), 5 mM glucose pH adjusted to 7.4). Assay plates were incubated for 1 hour at 37° C. The loading dye was then replaced with gluconate assay buffer containing probenecid.

Compounds diluted in gluconate buffer were transferred into the assay plates (25 μl/well) followed by incubation for 20 minutes at room temperature. The assay plates were then transferred to a Fluorometric Imaging Plate Reader (FLIPR), a baseline was read for twenty second capture, followed by the addition of 25 μl/well of channel activation solution in gluconate buffer—for KCa3.1 cells thallium (3.3 mM)/ionomycin(1 μM) was used and for the wild type, ionomycin only, then fluorescence was monitored for another 90 seconds.

The compounds I of the present invention exhibit $IC_{50}$ values in the thallium assay of 10 nM to 20 μM, preferably 10 nM to 1 μM for Thallium influx. The following table shows measured values for some selected compounds of the present invention.

| Example no | IC50 thallium (μM) |
| --- | --- |
| 1 | 0.86 |
| 2 | 0.83 |
| 3 | 0.63 |
| 4 | 3.14 |
| 5 | 0.66 |
| 5 | 1.14 |
| 6 | 1.34 |
| 7 | 0.72 |
| 8 | 7.15 |
| 9 | 6.05 |
| 10 | 1.9 |
| 11 | 0.25 |
| 12 | 1.1 |
| 13 | 0.34 |
| 14 | 3.6 |
| 15 | 0.7 |
| 16 | 1 |
| 17 | 0.88 |
| 18 | 3.7 |
| 19 | 0.74 |
| 20 | 2.2 |
| 21 | 0.65 |
| 22 | 0.6 |
| 24 | 1.48 |
| 23 | 1.96 |
| 25 | 10 |
| 26 | 9.2 |
| 27 | 6.7 |
| 28 | 0.77 |
| 29 | 6.7 |
| 30 | 17.5 |
| 31 | 7.54 |
| 32 | 0.6 |
| 33 | 1.56 |
| 34 | 6.7 |
| 35 | 0.45 |
| 36 | 6.6 |
| 37 | 4.9 |
| 38 | 1.6 |

| Example no | IC50 thallium (μM) |
| --- | --- |
| 39 | 11 |
| 40 | 6.9 |

Electrophysiology Patch Clamp

Compounds were tested using a PatchXpress® (Model 7000A, Molecular Devices, Union City Calif.) on CHO cells over-expressing h KCa3.1 at ChanTest Corporation, 14656 Neo Parkway, Cleveland, Ohio.

The compounds I of the present invention exhibit $IC_{50}$ values in the patch clamp assay of 10 nM to 10 μM, preferably 10 nM to 1 μM for patch clamp. The following table shows measured values for some selected compounds of the present invention.

| Example no | IC50 Ephys (μM) |
| --- | --- |
| 1 | 0.058 |
| 7 | 0.045 |
| 11 | 0.022 |
| 13 | 0.015 |
| 15 | 0.042 |
| 17 | 0.015 |
| 19 | 0.063 |
| 32 | 0.062 |

The invention claimed is:

1. A compound of formula (I):

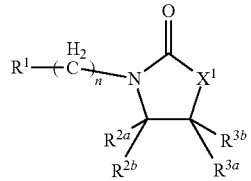

wherein $X^1$ is O or NH;

n is an integer between 1 to 4;

$R^1$ is hydrogen, cyano, —C(O)$R^{1a}$, —C(O)N$R^{1b}R^{1c}$, heteroaryl or $CH_2OH$;

$R^{1a}$ is hydrogen, $C_1$-$C_6$ alkyl, $C_1$-$C_6$ alkoxy, phenyl or heteroaryl;

$R^{1b}$ and $R^{1c}$ are each independently hydrogen, $C_1$-$C_6$ alkyl, phenyl or heteroaryl, wherein said $C_1$-$C_6$ alkyl, said phenyl or said heteoaryl are optionally substituted with one or more substituents independently selected from the group consisting of hydroxy, halogen, $C_1$-$C_6$ alkyl, $C_1$-$C_6$ alkoxy, halo$C_1$-$C_6$ alkyl and halo$C_1$-$C_6$ alkoxy;

$R^{2a}$ is hydrogen or $C_1$-$C_6$ alkyl;

$R^{2b}$ is halo$C_1$-$C_6$alkyl, $C_1$-$C_6$ alkyl, phenyl or heteroaryl, wherein said phenyl or said heteroaryl are optionally substituted with one or more substituents independently selected from the group consisting of hydroxy, halogen, $C_1$-C alkyl and halo$C_1$-$C_6$alkyl;

$R^{3a}$ and $R^{3b}$ are each phenyl optionally substituted with one or more substituents independently selected from the group consisting of halogen, $C_1$-$C_6$alkyl and halo$C_1$-$C_6$alkyl;

or pharmaceutically acceptable salts.

2. The compound according to claim 1, wherein $X^1$ is O.

3. The compound according to claim 1, wherein n is 1 or 2.

4. The compound according to claim 1, wherein $R^1$ is hydrogen, cyano, —C(O)$R^{1a}$, —C(O)N$R^{1b}R^{1c}$ or 1,2,4-triazolyl.

5. The compound according to claim 1, wherein $R^1$ is cyano, —C(O)$R^{1a}$, —C(O)N$R^{1b}R^{1c}$ or triazolyl.

6. The compound according to claim 1, wherein $R^1$ is cyano, —C(O)$R^{1a}$ or —C(O)N$R^{1b}R^{1c}$.

7. The compound according to claim 1, wherein $R^1$ is —C(O)$R^{1a}$ or —C(O)N$R^{1b}R^{1c}$.

8. The compound according to claim 1, wherein $R^{1a}$ is methoxy or ethoxy.

9. The compound according to claim 1, wherein $R^{1b}$ and $R^{1c}$ are each independently hydrogen, methyl or ethyl.

10. The compound according to claim 1, wherein $R^{2a}$ is hydrogen.

11. The compound according to claim 1, wherein $R^{2b}$ is perhalo$C_1$-$C_3$alkyl, $C_1$-$C_3$ alkyl, phenyl or heteroaryl, wherein said phenyl or said heteroaryl are optionally substituted with one or more substituents independently selected from the group consisting of hydroxy, halogen, $C_1$-$C_3$ alkyl and halo$C_1$-$C_3$alkyl.

12. The compound according to claim 1, wherein $R^{2b}$ is perhalo$C_1$-$C_3$alkyl, $C_1$-$C_3$ alkyl, phenyl or pyridinyl, wherein said phenyl or said pyridinyl are optionally substituted with one or two substituents independently selected from the group consisting of halogen, $C_1$-$C_3$ alkyl and halo$C_1$-$C_3$alkyl.

13. The compound according to claim 1, wherein $R^{2b}$ is phenyl or pyridinyl, wherein said phenyl or said pyridinyl are optionally substituted with one or two substituents independently selected from the group consisting of halogen and $C_1$-$C_3$ alkyl.

14. The compound according to claim 1, wherein $R^{2b}$ is phenyl optionally substituted with one or two substituents independently selected from the group consisting of halogen and $C_1$-$C_3$ alkyl.

15. The compound according to claim 1, wherein $R^{2b}$ is phenyl optionally substituted with one or two substituents independently selected from the group consisting of chloro, fluoro and methyl.

16. The compound according to claim 1, wherein $R^{3a}$ and $R^{3b}$ are each independently phenyl optionally substituted with one or more halogen.

17. The compound according to claim 1, The compound wherein $R^{3a}$ and $R^{3b}$ are the same and are phenyl optionally substituted with one or more chloro or fluoro.

18. The compound according to claim 1, wherein $R^{3a}$ and $R^{3b}$ are each independently phenyl optionally substituted with one to two chloro or fluoro.

19. The compound according to claim 10, wherein both $R^{3a}$ and $R^{3b}$ are phenyl substituted with one fluoro.

20. The compound according to claim 1, selected from:
2-[(S)-4-(2,4-Difluoro-phenyl)-5,5-bis-(4-fluoro-phenyl)-2-oxo-oxazolidin-3-yl]-acetamide;
2-[(S)-4,5,5-Tris-(4-fluoro-phenyl)-2-oxo-oxazolidin-3-yl]-acetamide;
2-[(S)-5,5-Bis-(4-fluoro-phenyl)-4-(2-fluoro-phenyl)-2-oxo-oxazolidin-3-yl]-acetamide;
2-[(S)-4,5,5-Tris-(2-fluoro-phenyl)-2-oxo-oxazolidin-3-yl]-acetamide;
2-[(S)-5,5-Bis-(3-fluoro-phenyl)-4-(2-fluoro-phenyl)-2-oxo-oxazolidin-3-yl]-acetamide;
2-[(S)-4-(2-Fluoro-phenyl)-2-oxo-5,5-diphenyl-oxazolidin-3-yl]-acetamide;
2-[(S)-4-(2-Chloro-phenyl)-5,5-bis-(4-fluoro-phenyl)-2-oxo-oxazolidin-3-yl]-acetamide;
(S)-methyl 2-(4-(2-fluorophenyl)-5,5-bis(4-fluorophenyl)-2-oxooxazolidin-3-yl)acetate;
(S)-2-(4-(2-fluorophenyl)-5,5-bis(4-fluorophenyl)-2-oxooxazolidin-3-yl)-N-methylacetamide;
(S)-2-(5,5-bis(3,4-difluorophenyl)-2-oxo-4-phenyloxazolidin-3-yl)acetamide;
and pharmaceutically acceptable salts thereof.

21. A pharmaceutical composition comprising the compound of claim 1 admixed with at least one pharmaceutically acceptable carrier, excipient or diluent.

* * * * *